US007598344B2

(12) United States Patent
Belcher et al.

(10) Patent No.: US 7,598,344 B2
(45) Date of Patent: Oct. 6, 2009

(54) COMPOSITION, METHOD AND USE OF BI-FUNCTIONAL BIOMATERIALS

(75) Inventors: Angela M. Belcher, Lexington, MA (US); Christine J. Schmidt, Austin, TX (US); Kiley P. H. Miller, Somerville, MA (US); Archit Sanghvi, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/654,623

(22) Filed: Sep. 4, 2003

(65) Prior Publication Data

US 2004/0127640 A1    Jul. 1, 2004

Related U.S. Application Data

(60) Provisional application No. 60/408,528, filed on Sep. 4, 2002.

(51) Int. Cl.
*C07K 7/00* (2006.01)
*C08G 63/48* (2006.01)
*C08G 63/91* (2006.01)
*A61K 38/31* (2006.01)

(52) U.S. Cl. ............... 530/327; 530/324; 530/325; 530/326; 530/350; 530/808; 530/815; 536/23.1; 525/54.1

(58) Field of Classification Search .............. 530/327, 530/324–326, 350, 808, 815; 536/231.1; 525/54.1
See application file for complete search history.

(56) References Cited

U.S. PATENT DOCUMENTS

| | | | |
|---|---|---|---|
| 4,929,389 A | 5/1990 | Aldissi | |
| 5,294,372 A | 3/1994 | Kochem et al. | |
| 5,401,537 A | 3/1995 | Kochem et al. | |
| 5,569,798 A | 10/1996 | Jackson | |
| 5,648,453 A | 7/1997 | Saida et al. | |
| 5,670,607 A | 9/1997 | Chen | |
| 5,688,873 A | 11/1997 | Saida et al. | |
| 5,739,305 A | 4/1998 | Cubicciotti | |
| 5,843,741 A | 12/1998 | Wong et al. | |
| 5,968,417 A | 10/1999 | Viswanathan | |
| 5,976,284 A | 11/1999 | Calvert et al. | |
| 6,095,148 A | 8/2000 | Shastri et al. | |
| 6,630,307 B2 * | 10/2003 | Bruchez et al. | ............... 435/6 |
| 6,815,078 B2 * | 11/2004 | Qiao et al. | ............... 428/478.2 |
| 6,989,267 B2 * | 1/2006 | Kim et al. | ............... 435/287.2 |
| 7,147,917 B2 * | 12/2006 | Adams et al. | ............... 428/403 |
| 2001/0055764 A1 * | 12/2001 | Empedocles et al. | ............... 435/6 |
| 2002/0022284 A1 | 2/2002 | Heeger et al. | |
| 2003/0068900 A1 | 4/2003 | Belcher et al. | |
| 2003/0073104 A1 | 4/2003 | Belcher et al. | |
| 2003/0113714 A1 | 6/2003 | Belcher et al. | |
| 2003/0148380 A1 | 8/2003 | Belcher et al. | |
| 2003/0185870 A1 * | 10/2003 | Grinstaff et al. | ............ 424/423 |
| 2004/0171139 A1 | 9/2004 | Belcher et al. | |

FOREIGN PATENT DOCUMENTS

| | | |
|---|---|---|
| WO | WO 03/078451 | 9/2003 |
| WO | WO 2004/033488 | 4/2004 |

OTHER PUBLICATIONS

Brott et al., "Ultrafast Holographic Nanopattering of Biocatalytically Formed Silica," Letters to Nature, vol. 413, Sep. 2001, pp. 291-293.
Chiang et al., "Electrical Conductivity in Doped Polycetylene," Physical Review Letters, vol. 39, No. 17, Oct. 24, 1977, pp. 1098-1101.
Chien, "Current Developments of Interest and Their Potential Applications," The Physical Approach: Implants, Drugs and Pharmaceutical Sciences, vol. 6, Marcel Dekker, Inc., 1978, pp. 321-341.
Diaz et al., "Electrochemical Polymerization of Pyrrole," J.C.S. Chem. Comm., 1979, pp. 635-636.
Dos Santos et al., "Elementary Excitations in Poly-Phenylene Imine, The Oxidized Form of Polyaniline," Synthetic Metals, vol. 29, Elsevier Sequoia, 1989, pp. E321-E327.
Dos Santos et al., "Nonlinear Excitation in Pernigraniline, The Oxidized Form of Polyaniline," Physical Review Letters, The American Physical Society, vol. 62, No. 21, May 22, 1989, pp. 2499-2502.
Genies et al., "Polyaniline: A Historical Survey," Synthetic Metals, vol. 36, Elsevier Sequoia, 1990, pp. 139-182.
Gibson et al., "Poly(1,6-Heptadiyne), a Free-Standing Polymer Film Dopable to High Electrical Conductivity," J. Am. Chem. Soc., vol. 105, American Chemical Society, 1983, pp. 4417-4431.
Ito et al., "Simultaneous Polymerization and Formation of Polyacetylene Film on The Surface of Concentrated Soluble Ziegler-Type Catalyst Solution" Journal of Polymer Science, vol. 12, John Wiley & Sons, Inc., 1974, pp. 11-20.
Ivory et al., Highly Conducting Charge-Transfer complexes of Poly(p-phenylene), Letters to the Editor, J. Chem. Phys, vol. 71, No. 3, American Institute of Physics, Aug. 1979, pp. 1506-1507.
Kanazawa et al., "Organic Metals': Polypyrrole, a Stable Synthetic 'Metallic' Polymer," J.C.S. Chem. Comm., 1979, pp. 854-855.
Kroschwitz, "Electrically Conductive Polymers," Concise Encyclopedia of Polymer Science and Engineering, John Wiley & Sons, pp. 298-300.

(Continued)

*Primary Examiner*—T. D. Wessendorf
(74) *Attorney, Agent, or Firm*—Foley & Lardner LLP

(57) ABSTRACT

The present invention includes a bifunctional specificity structure that includes a peptide linker having a first and a second binding domain, wherein the first binding domain is selective for a first biomaterial and the second binding domain is selective for a second biomaterial. The present invention also includes a method of making and identifying the bifunctional structure of the present invention and methods of using the same.

4 Claims, 23 Drawing Sheets

OTHER PUBLICATIONS

MacDiarmid et al., "Organic Metals and Semiconductors: The Chemistry of Polyacetylene, $(CH)_x$, and Its Derivatives," Synthetic Metals, Elsevier Sequoia, 1979, pp. 101-118.

Naik et al., "Silica-Precipitating Peptides Isolated From A Combinatorial Phage Display Peptide Library," Journal of Nanoscience and Nanotechnology, vol. 2, No. 1, American Scientific Publishers, 2002, pp. 95-100.

Naik et al., "Biomimetic Synthesis And Pattering of Silver Nanoparticles," Letters, Nature Materials, vol. 1, Nature Publishing Group, Nov. 2002, pp. 169-172.

Nigrey et al., "Electrochemistry of Polyacetylene, $(CH)_x$: Electrochemical Doping of $(CH)_x$ Films to the Metallic State," J.C. S. Chem. Comm., 1979, pp. 594-595.

Petrenko et al., "Phage Display for Detection of Biological Threat Agents," Journal of Microbiological Methods, vol. 53, Elsevier, 2003, pp. 253-262.

Rozinov et al., "Evolution of Peptides That Modulate The Spectral Qualities of Bound, Small-Molecule Fluorophores," Research Paper, Chemistry and Biology, vol. 5, No. 12, 1998, pp. 713-728.

Schott et al., "Introduction to Conjugated and Conducting Polymers," Organic Conductors Fundamentals and Applications, Marcel Dekker, Inc., 1994, pp. 495-538.

Shirakawa et al., "Synthesis of Electrically Conducting Organic Polymers: Halogen Derivatives of Polyacetylene, $(CH)_x$," J.C.S. Chem. Comm., 1977, pp. 578-580.

Tourillon et al., "New Electrochemically Generated Organic Conducting Polymers," J. Electroanal Chem., vol. 135, Elsevier Sequoia, 1982, pp. 173-178.

Venkatesh et al., "A Synthetic Peptide with Estrogen-Like Activity Derived From a Phage-Display Peptide Library," Peptides, vol. 23, Elsevier Science, Inc., 2000, pp. 573-580.

Yu et al., "Etude Experimentale de la Conductive en Courant Continu des Composes Macromoleculaires," Journal of Polymer Science: Part C, No. 16, 1967, pp. 2931-2942. See English abstract.

Fodor, S. P., et al., "Light-Directed, Spatially Addressable Parallel Chemical Synthesis", Science, 251(4995: pp. 767-773 (1991).

Foehr, E. D., et al., "NF-kappa B Signaling Both Cell Survival and Neurite Process Formation in Nerve Growth Factor-Stimulated PC12 Cells", J. Neurosci., 20(20): pp. 7556-7563 (2000). Schmidt, C. E., et al., "Acellular vascular tissues: natural biomaterials for tissue repair and tissue engineering", Biomaterials, 21(22): pp. 2215-2231 (2000).

Gebhardt, K., et al., "Adhesive peptides selected by phage display; characterization, applications and similarities with fibrinogen", Peptide Research, vol. 9, No. 6, pp. 269-278.

Goldman, R., et al., "Electric Fields and Proliferation in a Chronic Wound Model", Biolelectromag., vol. 17, No. 6, pp. 450-457 (1996).

Healy, K. E., "Molecular engineering of materials for bioreactivity", Curr. Opn. Sol. Sta. & Mater. Sci., vol. 4, pp. 381-387 (1999).

Hern, D. L., et al., "Incorporation of adhesion peptides into nonadhesive hydrogels useful for tissue resurfacing", J. Biomed. Mat. Res., vol. 39, No. 2, pp. 266-276 (1998).

Hu, J., et al., "Imaging of Single Exteded DNA Molecules on Flat (Aminopropyl)triethoxysilane-Mica by Atomic Force Microscopy", Langmuir, 12(7): pp. 1697-1700 (1996).

Kotwal, A., et al., "Electrical stimulation alters protein adsorption and nerve cell interactions with electrically conducting biomaterials", Biomaterials, 22(10): pp. 1055-1064 (2001).

Langer, R., "Drug Delivery: Drugs on Target", Science, 293(5527): pp. 58-59 (2001).

Lee, S., et al., "Ordering of Quantum Dots Using Genetically Engineered Viruses", Science, 296 (5569): pp. 892-895 (2002).

Millesi, H., "Progress in Peripheral Nerve Reconstruction", World J.Surg., vol. 14, pp. 733-747 (1990).

Parmley., S. F., et al., "Antibody-selectable filamentous fd phage vectors: affinity purification of target genes", Gene, 73(2): pp. 305-318 (1988).

Politis, M. J., et al. "The Short-term effects of delayed application of electric fields in the damaged rodent spinal cord", Neursug., vol. 25, No. 1, pp. 71-75 (1989).

Puleo, D. A., Biochemical Surface modification of Co-Cr-Mo, Biomaterials, vol. 17, pp. 217-222 (1996).

Quirk, R., et al., "Poly(L-lysine)-GRGDS as a biomimetic surface modifier for poly(lactic acid)", Biomaterials, vol. 22, pp. 865-872 (2001).

Rief, M., "Reversible Unfolding of Individual Titin Immunoglobulin Domains By AFM", Science, 276(5315): pp. 1109-1112 (1997).

Schmidt, C. E., et al., "Acellular vascular tissues: natural biomaterials for tissue repair and tissue engineering", Biomaterials, 21(22): pp. 2215-2231(2000).

Schmidt, C. E., et al., "Stimulation of neurite outgrowth using an electrically conducting polymer", Proc. Natl. Acad. Sci., 94(17): pp. 8948-8953 (1997).

Aaron, R. K., "Therapeutic Effects of Electromagnetic Fields in the Stimulation of Connective Tissue Repair", J. Cell. Biochemistry 52; pp. 42-46 (1993).

Barry, M. A., "Toward cell-targeting gene therapy vectors: selection of cell-binding peptides from random peptide-presenting phage libraries", Nature Medicine, 2(3): pp. 299-305 (1996).

Cao, X., et al., "Delivering Neuroactive Molecules From Biodegradable Microspheres for application in central nervous system disorders", Biomaterials, 20(4): pp. 329-339 (1999).

Ciombor, D. M., et al., "Influence of electromagnetic Fields on Endochondral Bone Formation", J. Cell. Biochem., 52(1): pp. 37-41 (1993).

Dee, K. C., et al., "Conditions which promote mineralization at the bone-implant interface: a model in vitro study", Biomaterials, vol. 17, pp. 209-215 (1996).

Devlin, J. J., "Random Peptide Libraries: a source of specific protein binding molecules", Science, 249(4967): pp. 404-406 (1990).

Diaz, A. F., et al., "Electrochemistry of Conducting Polypyrrole Films", J. Electroanal. Chem., 129: pp. 115-132 (1981).

Doorbar, J., et al., "Isolation of a peptide antagonist to the thrombin receptor using phage display", J. Mol. Biol., 244(4): pp. 361-369 (1994).

Fodor, S. P., et al., "Light-Directed, Spatially Addressable Parallel Chemical Synthesis", Science, 251(4995: pp. 767-773 (1991).

Foehr, E. D., et al., "NF-kappa B Signaling Both Cell Survival and Neurite Process Formation in Nerve Growth Factor-Stimulated PC12 Cells", J. Neurosci., 20(20): pp. 7556-7563 (2000). Schmidt, C. E., et al., "Acellular vascular tissues: natural biomaterials for tissue repair and tissue engineering", Biomaterials, 21(22): pp. 2215-2231 (2000).

Gebhardt, K., et al., "Adhesive peptides selected by phage display; characterization, applications and similarities with fibrinogen", Peptide Research, vol. 9, No. 6, pp. 269-278, 1996.

Goldman, R., et al., "Electric Fields and Proliferation in a Chronic Wound Model", Biolelectromag., vol. 17, No. 6, pp. 450-457 (1996).

Healy, K. E., "Molecular engineering of materials for bioreactivity", Curr. Opn. Sol. Sta. & Mater. Sci., vol. 4, pp. 381-387 (1999).

Hern, D. L., et al., "Incorporation of adhesion peptides into nonadhesive hydrogels useful for tissue resurfacing", J. Biomed. Mat. Res., vol. 39, No. 2, pp. 266-276 (1998).

Hu, J., et al., "Imaging of Single Exteded DNA Molecules on Flat (Aminopropyl)triethoxysilane-Mica by Atomic Force Microscopy", Langmuir, 12(7): pp. 1697-1700 (1996).

Kotwal, A., et al., "Electrical stimulation alters protein adsorption and nerve cell interactions with electrically conducting biomaterials", Biomaterials, 22(10): pp. 1055-1064 (2001).

Langer, R., "Drug Delivery: Drugs on Target", Science, 293(5527): pp. 58-59 (2001).

Lee, S., et al., "Ordering of Quantum Dots Using Genetically Engineered Viruses", Science, 296 (5569): pp. 892-895 (2002).

Millesi, H., "Progress in Peripheral Nerve Reconstruction", World J.Surg., vol. 14, pp. 733-747 (1990).

Parmley., S. F., et al., "Antibody-selectable filamentous fd phage vectors: affinity purification of target genes", Gene, 73(2): pp. 305-318 (1988).

Politis, M. J., et al. "The Short-term effects of delayed application of electric fields in the damaged rodent spinal cord", Neursug., vol. 25, No. 1, pp. 71-75 (1989).

Puleo, D. A., Biochemical Surface modification of Co-Cr-Mo, Biomaterials, vol. 17, pp. 217-222 (1996).

Quirk, R., et al., "Poly(L-lysine)-GRGDS as a biomimetic surface modifier for poly(lactic acid)", Biomaterials, vol. 22, pp. 865-872 (2001).

Rief, M., "Reversible Unfolding of Individual Titin Immunoglobulin Domains By AFM", Science, 276(5315): pp. 1109-1112 (1997).

Schmidt, C. E., et al., "Acellular vascular tissues: natural biomaterials for tissue repair and tissue engineering", Biomaterials, 21(22): pp. 2215-2231(2000).

Schmidt, C. E., et al., "Stimulation of neurite outgrowth using an electrically conducting polymer", Proc. Natl. Acad. Sci., 94(17): pp. 8948-8953 (1997).

Schultz, J. S., "Biosensors", Scientific Am., 265(2): pp. 64-69 (1991).

Scott, J. K., et al., "A Family of Concanavalin A-binding peptides frim a hexapeptide epitope library" Proc. Natl. Acad. Sci., vol. 89, pp. 5398-5402 (1992).

Shastri, V. R., et al., "Polypyrrole—A Potential Candidate for Stimulated Nerve Regeneration", Mater. Res. Soc. Symp. Proc., vol. 414, pp. 113-118 (1996).

Smith, M. M., et al., "Rapid Identification of Highly Active and Selective Substrates for Stromelysin and Matrilysin Using Bacteriophage Peptide Display Libraries", J. Biol. Chem., 270(1): pp. 6440-6449 (1995).

Tong, Y. W., et al., "Peptide Surface Modification of Poly(tetrafluoroethylene-co-hexafluoropropylene) Enhances Its Interaction with Central Nervous System Neurons", J. Biomed. Mat. Res., vol. 42, No. 1, pp. 85-95 (1998).

Wanner, I. B., et al., "N-Cadherin Mediates Axon-Aligned Process Growth and Cell-Cell Interaction in Rat Schwann Cells", J. Neurosci., 22(10): pp. 4066-4079 (2002).

Whaley, S. R., et al., "Selection of Peptides with Semiconductor Binding Specificity for Directed Nanocrystal Assembly", Nature, 405(6787): pp. 665-668 (2000).

Xiao, S., et al., "Covalent Attachment of Cell-Adhesive, (Arg-Gly-Asp)-Containing Peptides to Titanium Surfaces", Langmuir, vol. 14, pp. 5507-5516 (1998).

Zanakis, M. F., "Differential effects of various electrical parameters on peripheral and central nerve regeneration", Acupuncutre and Electro-Therapeutics Res., vol. 15, No. 3-4, pp. 185-191 (1990).

Zhang, S., et al., "Peptide self-assembly in Functional Polymer Science and Engineering", Reac. & Func. Polym., 41: pp. 91-102 (1999).

Miller, K. P., "Fabrication of Novel Interactive Biomaterials via Peptide Integration for Tissue Engineering Applications", Thesis, Univ. of Texas at Austin (2002).

International Search Report dated Aug. 30, 2004.

US 5,382,513, 01/1995, Lam et al. (withdrawn)

* cited by examiner

| | | | | | | | | | | | | |
|---|---|---|---|---|---|---|---|---|---|---|---|---|
| T31 | T | H | R | T | S | T | L | D | Y | F | V | I | SEQ ID NO.:1 |
| T32 | T | H | R | T | S | T | L | D | Y | F | V | I | SEQ ID NO.:1 |
| T33 | T | H | R | T | S | T | L | D | Y | F | V | I | SEQ ID NO.:1 |
| T34 | T | H | R | T | S | T | L | D | Y | F | V | I | SEQ ID NO.:1 |
| T36 | T | I | K | M | H | T | L | S | Y | T | G | L | SEQ ID NO.:2 |
| T37 | T | H | R | T | S | T | L | D | Y | F | V | I | SEQ ID NO.:1 |
| T38 | T | H | R | T | S | T | L | D | Y | F | V | I | SEQ ID NO.:1 |
| T41 | T | H | R | T | S | T | L | D | Y | F | V | I | SEQ ID NO.:1 |
| T42 | T | H | R | T | S | T | L | D | Y | F | V | I | SEQ ID NO.:1 |
| T43 | S | H | K | Y | P | K | P | P | Y | F | H | W | SEQ ID NO.:3 |
| T44 | T | H | R | T | S | T | L | D | Y | F | V | I | SEQ ID NO.:1 |
| T45 | T | H | R | T | S | T | L | D | Y | F | V | I | SEQ ID NO.:1 |
| T46 | T | H | R | T | S | T | L | D | Y | F | V | I | SEQ ID NO.:1 |
| T47 | T | H | R | T | S | T | L | D | Y | F | V | I | SEQ ID NO.:1 |
| T48 | T | H | R | T | S | T | L | D | Y | F | V | I | SEQ ID NO.:1 |
| T49 | T | H | R | T | S | T | L | D | Y | F | V | I | SEQ ID NO.:1 |
| T410 | T | H | R | T | S | T | L | D | Y | F | V | I | SEQ ID NO.:1 |
| T51 | T | H | R | T | S | T | L | D | Y | F | V | I | SEQ ID NO.:1 |
| T52 | T | H | R | T | S | T | L | D | Y | F | V | I | SEQ ID NO.:1 |
| T53 | T | H | R | T | S | T | L | D | Y | F | V | I | SEQ ID NO.:1 |
| T54 | T | H | R | T | S | T | L | D | Y | F | V | I | SEQ ID NO.:1 |
| T55 | T | H | R | T | S | T | L | D | Y | F | V | I | SEQ ID NO.:1 |
| T56 | T | H | R | T | S | T | L | D | Y | F | V | I | SEQ ID NO.:1 |
| T57 | T | H | R | T | S | T | L | D | Y | F | V | I | SEQ ID NO.:1 |
| T58 | T | H | R | T | S | T | L | D | Y | F | V | I | SEQ ID NO.:1 |
| T59 | T | H | R | T | S | T | L | D | Y | F | V | I | SEQ ID NO.:1 |

FIG. 5

Amino acid per position (%)

| | | | | | | | | | | | | |
|---|---|---|---|---|---|---|---|---|---|---|---|---|
| F | 0 | 0 | 0 | 0 | 0 | 0 | 0 | 0 | 0 | 96 | 0 | 0 |
| W | 0 | 0 | 0 | 0 | 0 | 0 | 0 | 0 | 0 | 0 | 0 | 4 |
| M | 0 | 0 | 0 | 4 | 0 | 0 | 0 | 0 | 0 | 0 | 0 | 0 |
| P | 0 | 0 | 0 | 0 | 4 | 0 | 4 | 4 | 0 | 0 | 0 | 0 |
| H | 0 | 96 | 0 | 0 | 4 | 0 | 0 | 0 | 0 | 0 | 4 | 0 |
| K | 0 | 0 | 8 | 0 | 0 | 4 | 0 | 0 | 0 | 0 | 0 | 0 |
| R | 0 | 0 | 92 | 0 | 0 | 0 | 0 | 0 | 0 | 0 | 0 | 0 |
| N | 0 | 0 | 0 | 0 | 0 | 0 | 0 | 0 | 0 | 0 | 0 | 0 |
| Q | 0 | 0 | 0 | 0 | 0 | 0 | 0 | 0 | 0 | 0 | 0 | 0 |
| E | 0 | 0 | 0 | 0 | 0 | 0 | 0 | 0 | 0 | 0 | 0 | 0 |
| D | 0 | 0 | 0 | 0 | 0 | 0 | 0 | 92 | 0 | 0 | 0 | 0 |
| V | 0 | 0 | 0 | 0 | 0 | 0 | 0 | 0 | 0 | 0 | 92 | 0 |
| G | 0 | 0 | 0 | 0 | 0 | 0 | 0 | 0 | 0 | 0 | 4 | 0 |
| A | 0 | 0 | 0 | 0 | 0 | 0 | 0 | 0 | 0 | 0 | 0 | 0 |
| I | 0 | 4 | 0 | 0 | 0 | 0 | 0 | 0 | 0 | 0 | 0 | 92 |
| L | 0 | 0 | 0 | 0 | 0 | 0 | 96 | 0 | 0 | 0 | 0 | 4 |
| T | 96 | 0 | 0 | 92 | 0 | 96 | 0 | 0 | 0 | 4 | 0 | 0 |
| S | 4 | 0 | 0 | 0 | 92 | 0 | 0 | 4 | 0 | 0 | 0 | 0 |
| Y | 0 | 0 | 0 | 4 | 0 | 0 | 0 | 0 | 100 | 0 | 0 | 0 |
| Max percent | 96 | 96 | 92 | 92 | 92 | 96 | 96 | 92 | 100 | 96 | 92 | 92 |
| Predominant (SEQ ID NO.:1) | T | H | R | T | S | T | L | D | Y | F | V | I |

|  | 1 | 2 | 3 | 4 | 5 | 6 |
|---|---|---|---|---|---|---|
| Basic | 0% | 96% | 100% | 0% | 4% | 4% |
| Acidic | 0% | 0% | 0% | 0% | 0% | 0% |
| $H_2O$ Phobics | 0% | 4% | 0% | 0% | 0% | 0% |
| Hydroxyl | 100% | 0% | 0% | 96% | 92% | 96% |
| Aromatic | 0% | 0% | 0% | 0% | 0% | 0% |
| Amides | 0% | 0% | 0% | 0% | 0% | 0% |
| Met | 0% | 0% | 0% | 4% | 0% | 0% |
| Pro | 0% | 0% | 0% | 0% | 4% | 0% |

B

|  | 7 | 8 | 9 | 10 | 11 | 12 | total | library |
|---|---|---|---|---|---|---|---|---|
| Basic | 0% | 0% | 0% | 0% | 4% | 0% | 17.3% | 13.8% |
| Acidic | 0% | 92% | 0% | 0% | 0% | 0% | 7.7% | 5.9% |
| $H_2O$ Phobics | 96% | 0% | 0% | 0% | 96% | 96% | 24.4% | 25.2% |
| Hydroxyl | 0% | 4% | 100% | 4% | 0% | 0% | 41.0% | 24.7% |
| Aromatic | 0% | 0% | 0% | 96% | 0% | 4% | 8.3% | 5.5% |
| Amides | 0% | 0% | 0% | 0% | 0% | 0% | 0.0% | 9.7% |
| Met | 0% | 0% | 0% | 0% | 0% | 0% | 0.3% | 2.6% |
| Pro | 4% | 4% | 0% | 0% | 0% | 0% | 1.0% | 12.2% |

| P122-1 | V | F | T | A | P | A | R | L | I | T | P | L | SEQ ID NO.:5 |
| P122-2 | S | G | H | M | Q | P | V | T | R | P | P | A | SEQ ID NO.:6 |
| P123-1 | S | F | P | D | T | Y | V | R | V | K | P | A | SEQ ID NO.:7 |
| P123-2 | I | P | H | S | Q | V | T | M | R | G | L | P | SEQ ID NO.:8 |
| P123-3 | T | S | M | Q | L | S | M | E | H | K | L | S | SEQ ID NO.:9 |
| P123-8 | H | F | N | V | R | H | T | I | P | T | H | L | SEQ ID NO.:10 |
| P123-9 | M | P | T | T | W | S | T | T | L | Q | Y | H | SEQ ID NO.:11 |
| P123-10 | S | T | N | L | D | P | G | L | A | P | L | P | SEQ ID NO.:12 |
| P123-11 | G | Q | A | H | Y | K | I | A | T | G | E | A | SEQ ID NO.:13 |
| P123-12 | I | K | P | H | M | P | P | S | D | W | P | S | SEQ ID NO.:14 |
| P123-13 | M | P | T | T | W | S | T | T | L | Q | Y | H | SEQ ID NO.:11 |
| P124-1 | S | T | N | L | D | P | G | L | A | P | L | P | SEQ ID NO.:12 |
| P124-2 | G | Q | A | H | Y | K | I | A | T | G | E | A | SEQ ID NO.:13 |
| P124-3 | S | F | P | D | T | Y | V | R | V | K | P | A | SEQ ID NO.:7 |
| P124-4 | S | F | P | D | T | Y | V | R | V | K | P | A | SEQ ID NO.:7 |
| P124-5 | I | K | P | H | M | P | P | S | D | W | P | S | SEQ ID NO.:14 |

FIG. 11

| Amino acid per position (%) | | | | | | | | | | | | |
|---|---|---|---|---|---|---|---|---|---|---|---|---|
| F | 0 | 31 | 0 | 0 | 0 | 0 | 0 | 0 | 0 | 0 | 0 | 0 |
| W | 0 | 0 | 0 | 0 | 13 | 0 | 0 | 0 | 0 | 13 | 0 | 0 |
| M | 13 | 0 | 6.3 | 6.3 | 13 | 0 | 6.3 | 6.3 | 0 | 0 | 0 | 0 |
| P | 0 | 19 | 31 | 0 | 6.3 | 31 | 13 | 0 | 6.3 | 19 | 44 | 19 |
| H | 6.3 | 0 | 13 | 25 | 0 | 6.3 | 0 | 0 | 6.3 | 0 | 6.3 | 13 |
| K | 0 | 13 | 0 | 0 | 0 | 13 | 0 | 0 | 0 | 25 | 0 | 0 |
| R | 0 | 0 | 0 | 0 | 6.3 | 0 | 6.3 | 19 | 13 | 0 | 0 | 0 |
| N | 0 | 0 | 19 | 0 | 0 | 0 | 0 | 0 | 0 | 0 | 0 | 0 |
| Q | 0 | 13 | 0 | 6.3 | 13 | 0 | 0 | 0 | 0 | 13 | 0 | 0 |
| E | 0 | 0 | 0 | 0 | 0 | 0 | 0 | 6.3 | 0 | 0 | 13 | 0 |
| D | 0 | 0 | 0 | 19 | 13 | 0 | 0 | 0 | 13 | 0 | 0 | 0 |
| V | 6.3 | 0 | 0 | 6.3 | 0 | 6.3 | 25 | 0 | 19 | 0 | 0 | 0 |
| G | 13 | 6.3 | 0 | 0 | 0 | 0 | 13 | 0 | 0 | 19 | 0 | 0 |
| A | 0 | 0 | 13 | 6.3 | 0 | 6.3 | 0 | 13 | 13 | 0 | 0 | 38 |
| I | 19 | 0 | 0 | 0 | 0 | 0 | 13 | 6.3 | 6.3 | 0 | 0 | 0 |
| L | 0 | 0 | 0 | 13 | 6.3 | 0 | 0 | 19 | 13 | 0 | 25 | 13 |
| T | 6.3 | 13 | 19 | 13 | 19 | 0 | 25 | 19 | 13 | 13 | 0 | 0 |
| S | 38 | 6.3 | 0 | 6.3 | 0 | 19 | 0 | 13 | 0 | 0 | 0 | 19 |
| Y | 0 | 0 | 0 | 0 | 13 | 19 | 0 | 0 | 0 | 0 | 13 | 0 |
| Max percent | 38 | 31 | 31 | 25 | 19 | 31 | 25 | 19 | 19 | 25 | 44 | 38 |
| Predominant (SEQ ID NO.:7) | S | F | P | D | T | Y | V | R | V | K | P | A |

|  | 1 | 2 | 3 | 4 | 5 | 6 |
|---|---|---|---|---|---|---|
| Basic | 6% | 13% | 13% | 25% | 6% | 19% |
| Acidic | 0% | 0% | 0% | 19% | 13% | 0% |
| $H_2O$ Phobics | 38% | 6% | 13% | 25% | 6% | 13% |
| Hydroxyl | 44% | 19% | 19% | 19% | 31% | 38% |
| Aromatic | 0% | 31% | 0% | 0% | 13% | 0% |
| Amides | 0% | 13% | 19% | 6% | 13% | 0% |
| Met | 13% | 0% | 6% | 6% | 13% | 0% |
| Pro | 0% | 19% | 31% | 0% | 6% | 31% |

B

|  | 7 | 8 | 9 | 10 | 11 | 12 | total | library |
|---|---|---|---|---|---|---|---|---|
| Basic | 6% | 19% | 19% | 25% | 6% | 13% | 14.1% | 13.8% |
| Acidic | 0% | 6% | 13% | 0% | 13% | 0% | 5.2% | 5.9% |
| $H_2O$ Phobics | 50% | 38% | 50% | 19% | 25% | 50% | 27.6% | 25.2% |
| Hydroxyl | 25% | 31% | 13% | 13% | 13% | 19% | 23.4% | 24.7% |
| Aromatic | 0% | 0% | 0% | 13% | 0% | 0% | 4.7% | 5.5% |
| Amides | 0% | 0% | 0% | 13% | 0% | 0% | 5.2% | 9.7% |
| Met | 6% | 6% | 0% | 0% | 0% | 0% | 4.2% | 2.6% |
| Pro | 13% | 0% | 6% | 19% | 44% | 19% | 15.6% | 12.2% |

FIG. 13

| | | | | | | | | | | | |
|---|---|---|---|---|---|---|---|---|---|---|---|
| P32 | K | P | L | H | S | N | K | Y | Y | D | R | Y | SEQ ID NO.:15 |
| P33 | K | P | L | H | S | N | K | Y | Y | D | R | Y | SEQ ID NO.:15 |
| P34 | K | P | L | H | S | N | K | Y | Y | D | R | Y | SEQ ID NO.:15 |
| P35 | K | P | L | H | S | N | K | Y | Y | D | R | Y | SEQ ID NO.:15 |
| P36 | K | P | L | H | S | N | K | Y | Y | D | R | Y | SEQ ID NO.:15 |
| P37 | T | S | K | L | P | T | W | V | L | T | S | S | SEQ ID NO.:16 |
| P38 | F | N | P | H | Q | F | I | K | P | P | K | K | SEQ ID NO.:17 |
| P39 | T | S | K | L | P | T | W | V | L | T | S | S | SEQ ID NO.:16 |
| P310 | K | P | L | H | S | N | K | Y | Y | D | R | Y | SEQ ID NO.:15 |
| P41 | V | A | A | P | A | K | A | T | M | S | S | T | SEQ ID NO.:18 |
| P42 | K | P | L | H | S | N | K | Y | Y | D | R | Y | SEQ ID NO.:15 |
| P43 | V | A | A | P | A | K | A | T | M | S | S | T | SEQ ID NO.:18 |
| P45 | V | A | A | P | A | K | A | T | M | S | S | T | SEQ ID NO.:18 |
| P46 | V | A | A | P | A | K | A | T | M | S | S | T | SEQ ID NO.:18 |
| P47 | K | P | L | H | S | N | K | Y | Y | D | R | Y | SEQ ID NO.:15 |
| P48 | N | H | H | H | Q | P | L | A | R | N | Q | S | SEQ ID NO.:19 |
| P410 | V | A | A | P | A | K | A | T | M | S | S | T | SEQ ID NO.:18 |
| P51 | K | P | L | H | S | N | K | Y | Y | D | R | Y | SEQ ID NO.:15 |
| P52 | K | P | L | H | S | N | K | Y | Y | D | R | Y | SEQ ID NO.:15 |
| P53 | K | P | L | H | S | N | K | Y | Y | D | R | Y | SEQ ID NO.:15 |
| P54 | T | L | K | H | K | L | P | H | Q | T | R | W | SEQ ID NO.:19 |
| P55 | K | P | L | H | S | N | K | Y | Y | D | R | Y | SEQ ID NO.:15 |
| P56 | K | P | A | S | F | E | K | V | L | D | S | V | SEQ ID NO.:20 |
| P57 | V | A | A | P | A | K | A | T | M | S | S | T | SEQ ID NO.:18 |
| P58 | K | P | A | S | F | E | K | V | L | D | S | V | SEQ ID NO.:20 |
| P59 | M | H | H | H | Q | P | L | A | R | M | Q | S | SEQ ID NO.:21 |
| P510 | K | I | A | L | M | P | W | P | S | V | S | M | SEQ ID NO.:22 |

FIG. 14

| Amino acid per position (%) | | | | | | | | | | | | |
|---|---|---|---|---|---|---|---|---|---|---|---|---|
| F | 3.7 | 0 | 0 | 0 | 7.4 | 3.7 | 0 | 0 | 0 | 0 | 0 | 0 |
| W | 0 | 0 | 0 | 0 | 0 | 0 | 11 | 0 | 0 | 0 | 0 | 3.7 |
| M | 3.7 | 0 | 0 | 0 | 3.7 | 0 | 0 | 0 | 22 | 3.7 | 0 | 3.7 |
| P | 0 | 52 | 3.7 | 22 | 7.4 | 11 | 3.7 | 3.7 | 3.7 | 3.7 | 0 | 0 |
| H | 0 | 7.4 | 7.4 | 59 | 0 | 0 | 0 | 3.7 | 0 | 0 | 0 | 0 |
| K | 56 | 0 | 11 | 0 | 3.7 | 22 | 52 | 3.7 | 0 | 0 | 3.7 | 3.7 |
| R | 0 | 0 | 0 | 0 | 0 | 0 | 0 | 0 | 7.4 | 0 | 48 | 0 |
| N | 3.7 | 3.7 | 0 | 0 | 0 | 44 | 0 | 0 | 0 | 3.7 | 0 | 0 |
| Q | 0 | 0 | 0 | 0 | 11 | 0 | 0 | 0 | 3.7 | 0 | 7.4 | 0 |
| E | 0 | 0 | 0 | 0 | 0 | 7.4 | 0 | 0 | 0 | 0 | 0 | 0 |
| D | 0 | 0 | 0 | 0 | 0 | 0 | 0 | 0 | 0 | 52 | 0 | 0 |
| V | 22 | 0 | 0 | 0 | 0 | 0 | 0 | 15 | 0 | 3.7 | 0 | 7.4 |
| G | 0 | 0 | 0 | 0 | 0 | 0 | 0 | 0 | 0 | 0 | 0 | 0 |
| A | 0 | 22 | 33 | 0 | 22 | 0 | 22 | 7.4 | 0 | 0 | 0 | 0 |
| I | 0 | 3.7 | 0 | 0 | 0 | 0 | 3.7 | 0 | 0 | 0 | 0 | 0 |
| L | 0 | 3.7 | 44 | 11 | 0 | 3.7 | 7.4 | 0 | 15 | 0 | 0 | 0 |
| T | 11 | 0 | 0 | 0 | 0 | 7.4 | 0 | 22 | 0 | 11 | 0 | 22 |
| S | 0 | 7.4 | 0 | 7.4 | 44 | 0 | 0 | 0 | 3.7 | 22 | 41 | 15 |
| Y | 0 | 0 | 0 | 0 | 0 | 0 | 0 | 44 | 44 | 0 | 0 | 44 |
| Max percent | 56 | 52 | 44 | 59 | 44 | 44 | 52 | 44 | 44 | 52 | 48 | 44 |
| Predominant (SEQ ID NO.:15) | K | P | L | H | S | N | K | Y | Y | D | R | Y |

|  | 1 | 2 | 3 | 4 | 5 | 6 |
|---|---|---|---|---|---|---|
| Basic | 56% | 7% | 19% | 59% | 4% | 22% |
| Acidic | 0% | 0% | 0% | 0% | 0% | 7% |
| H₂0 Phobics | 22% | 30% | 78% | 11% | 22% | 4% |
| Hydroxyl | 11% | 7% | 0% | 7% | 44% | 7% |
| Aromatic | 4% | 0% | 0% | 0% | 7% | 4% |
| Amides | 4% | 4% | 0% | 0% | 11% | 44% |
| Met | 4% | 0% | 0% | 0% | 4% | 0% |
| Pro | 0% | 52% | 4% | 22% | 7% | 11% |

B

|  | 7 | 8 | 9 | 10 | 11 | 12 | total | library |
|---|---|---|---|---|---|---|---|---|
| Basic | 52% | 7% | 7% | 0% | 52% | 4% | 24.1% | 13.8% |
| Acidic | 0% | 0% | 0% | 52% | 0% | 0% | 4.9% | 5.9% |
| H₂0 Phobics | 33% | 22% | 15% | 4% | 0% | 7% | 20.7% | 25.2% |
| Hydroxyl | 0% | 67% | 48% | 33% | 41% | 81% | 29.0% | 24.7% |
| Aromatic | 11% | 0% | 0% | 0% | 0% | 4% | 2.5% | 5.5% |
| Amides | 0% | 0% | 4% | 4% | 7% | 0% | 6.5% | 9.7% |
| Met | 0% | 0% | 22% | 4% | 0% | 4% | 3.1% | 2.6% |
| Pro | 4% | 4% | 4% | 4% | 0% | 0% | 9.3% | 12.2% |

FIG. 16

```
                          SEQUENCE LISTING

<160> NUMBER OF SEQ ID NOS: 28

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 1

Thr His Arg Thr Ser Thr Leu Asp Tyr Phe Val Ile
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 2

Thr Ile Lys Met His Thr Leu Ser Tyr Thr Gly Leu
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 3

Ser His Lys Tyr Pro Lys Pro Pro Tyr Phe His Trp
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 4

Ile Glu His Pro Lys Thr Pro Asp Ser His Ser Arg
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 5

Val Phe Thr Ala Pro Ala Arg Leu Ile Thr Pro Leu
```

```
                    1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 6

Ser Gly His Met Gln Pro Val Thr Arg Pro Pro Ala
 1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 7

Ser Phe Pro Asp Thr Tyr Val Arg Val Lys Pro Ala
 1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 8

Ile Pro His Ser Gln Val Thr Met Arg Gly Leu Pro
 1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 9

Thr Ser Met Gln Leu Ser Asn Glu His Lys Leu Ser
 1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 10

His Phe Asn Val Arg His Thr Ile Pro Thr His Leu
 1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 11

Met Pro Thr Thr Trp Ser Thr Thr Leu Gln Tyr His
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Thr Asn Leu Asp Pro Gly Leu Ala Pro Leu Pro
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gln Ala His Tyr Lys Ile Ala Thr Gly Glu Ala
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Lys Pro His Met Pro Pro Ser Asp Trp Pro Ser
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Pro Leu His Ser Asn Lys Tyr Tyr Asp Arg Tyr
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Ser Lys Leu Pro Thr Trp Val Leu Thr Ser Ser
1               5                   10

<210> SEQ ID NO 17

```
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 17

Phe Asn Pro His Gln Phe Ile Lys Pro Pro Lys Lys
  1               5                  10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 18

Val Ala Ala Pro Ala Lys Ala Thr Met Ser Ser Thr
  1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 19

Asn His His His Gln Pro Leu Ala Arg Asn Gln Ser
  1               5                  10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 20

Lys Pro Ala Ser Phe Glu Lys Val Leu Asp Ser Val
  1               5                  10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 21

Met His His His Gln Pro Leu Ala Arg Met Gln Ser
  1               5                  10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
                        peptide

<400> SEQUENCE: 22
```

```
Lys Ile Ala Leu Met Pro Trp Pro Ser Val Ser Met
 1               5                  10
```

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Gly Arg Gly Asp Ser
 1               5
```

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Thr His Arg Thr Ser Thr Leu Asp Tyr Phe Val Ile Arg Gly Asp
 1               5                  10                  15
```

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Ala Ile Pro Val Ala Asn Asn Trp Gln Pro Leu Pro
 1               5                  10
```

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Glu His Glu Glu Pro Asp Leu Arg Leu Ala Arg Phe
 1               5                  10
```

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Ser Ala Asn Arg Ile Pro Leu Leu Pro Leu Asn Val
 1               5                  10
```

<210> SEQ ID NO 28
<211> LENGTH: 12
<212> TYPE: PRT
<213> ORGANISM: Artificial Sequence
<220> FEATURE:

```
-continued

<223> OTHER INFORMATION: Description of Artificial Sequence: Synthetic
                        peptide

<400> SEQUENCE: 28

Ala Arg Met Pro Ala Asn Leu Thr Val Gly Trp Ala
 1               5                  10
```

COMPOSITION, METHOD AND USE OF BI-FUNCTIONAL BIOMATERIALS

RELATED APPLICATIONS

This patent application claims benefit of provisional application No. 60/408,528 filed Sep. 4, 2002 to Belcher et al. which is hereby incorporated by reference in its entirety.

STATEMENT OF GOVERNMENT SUPPORT

The United States Federal Government may have certain rights in this invention. The subject matter of the application was carried out in part under Federal Government grant number CTS-0103473 from the National Science Foundation (NSF), Nanoscale Interdisciplinary Research Teams (NIRT).

TECHNICAL FIELD OF THE INVENTION

The present invention relates in general to the field of polymer chemistry, and more particularly to biologically modified polymers for use as biomaterials.

BACKGROUND OF THE INVENTION

Without limiting the scope of the invention, its background is described in connection with the development of biological materials (biomaterials, hereafter) by incorporating polymers with organic or biologic substituents (bi-functional biomaterials, hereafter). A nucleotide and/or amino acid sequence listing is incorporated by reference of the material on computer readable form.

Heretofore, in this field, the means of developing biologic materials has taken a variety of approaches, wherein traditionally non-biologic (i.e., non-organic) materials are modified in one or more ways to present biologic features that resemble or are recognized by natural biologic tissue (i.e., organ tissue). Modifications have included the use of protein adsorption and self assembly, synthesis of novel graft-co-polymers with the desired functional groups, and direct covalent surface modifications. Ultimately, the goal of manufacturing such biologic materials is to create a biomaterial that is flexible enough to adapt to changes in molecular design, is easy to synthesize, and can be applied to many different biologic uses (e.g., claudication, implantation, transplantation, biologic regeneration, growth, and as biologic replacements, modifications, or substitutions).

Recent investigations into creating biologic materials include the use of a microfabrication technique. Here, proteins and other molecular structures (including cells and/or tissue) are attached to the surface of a material that exhibits biologic properties (e.g., binds to one ore more biologic or organic compounds); the attachment is generally through nonspecific or specific recognition of the protein or other molecular structures to the material. For example, microcontact printing with a PDMS stamp is used to create micropatterns on the surface of a material. In the second stage, proteins or other molecular structures are adsorbed to the solid surface of the material. The unfortunate consequence of using such a technique is that the adsorption is nonuniform and creates irregular surfaces, much of which does not exhibit the necessary biologic properties that were initially desired. This is because the process is largely dependent upon non-specific interactions between the molecular structure and the material surface and these non-specific interactions result in less than optimal surfaces with randomly oriented molecules.

Others have engineered polymer surfaces to a material, using engineered polymers that may even control the adhesion of molecular structures to the polymer surface and are thought to be able to be used to attract one or more cells to the surface while maintaining the phenotypic expression of the cells. The drawback is that few polymers really have suitable functional groups that are able to covalently attach to a biologic structure. This fundamental flaw limits the use of a polymer as a biologic surface unless it is also modified to become more attractive to one or more biologic structures (e.g., organic compounds, biologic compounds, cells, tissue, etc.). Common approaches to functionally modifying a polymer include introducing reactive groups (e.g., poly(L-lysine)) at existing polymer surfaces by incorporating monomer units into the polymer backbone. Such approaches, however, are cost prohibitive by requiring complicated synthetic pathways and do not create uniform biomaterial surfaces (i.e., a surface containing one or more biologic structure).

An alternative method is a silanization technique that immobilizes peptides on the surface of a material. The method was demonstrated by depositing a silane film with terminal functional groups on a titanium oxide surface. In addition, the resulting surface could be further modified with different bi-functional linkers, eventually leading to the covalent attachment of a peptide sequence such as Arg-Gly-Asp (RGD)—a cellular recognition sequence used by several biologic proteins. The technique was also altered using different silane-like compounds such as aminosilane. Accordingly, a number of reactions with bi-functional linkers were performed, including: (a) glutaraldehyde to yield a linkage between the aldehyde imine and the peptide amine; and (b) aminosilane with a mixture of peptides and carbodiimides to yield a linkage between the amide and peptide carboxyl groups. These reactions were limited, however, in their ability to create specific peptide attachments at one or more defined sites. Consequently, unordered and nonuniform surfaces are produced.

Subsequent surface modification techniques have been used to create biologic materials with specific binding surfaces. For example, one technique was developed to create a neural surface (e.g., similar to the extracellular matrix of nervous tissue) using a polymer coupled to peptides. Here, poly(tetrafluroethylene-co-hexafluoropropylene) was reduced with sodium naphthalide to introduce carbon-carbon double bonds at the surface (e.g., a carbon-like film) and the reduced surface was then further modified to introduce hydroxyl groups (e.g., with hydroboration/oxidation) or carboxylic acid groups (e.g., through oxidation). The polymer, thus, contains either a hydroxyl (—$CH_x$OH) or carboxylic acid (—COOH) surface that could be coupled to one or more peptides. In fact, the attachment of 5- and 6-mer peptides was found to promote neurite extension (i.e., modified growth).

Materials with surfaces that resist protein adsorption and fouling have also been developed. These materials may be further modified with biologic components to promote specific molecular and/or cellular interactions. Polymers such as poly(ethylene glycol) or PEG that resist protein binding are suitable to use for these modifications. In addition, peptides such as those containing RGD sequences (e.g., acrylamidoyl peptides) may be incorporated into mixtures of PEG diacrylate to create a peptide-modified polymer. Unfortunately, this technique is unable to control the spatial orientation of peptides on the material (i.e., polymer) surface and only works with biologic structures of limited type and size. This type of modification is limited to polymers that have the ability for Pegylation, which can be important for immobilization of peptide via covalent reactions.

As evidenced by the above, current techniques are unable to create biologic materials with functional surfaces, that is surfaces that displays properties that allow for and promote interactions between the surface and another biologic structure (e.g., nucleic acid, protein, cell, tissue, organ, chromophore, etc.). There is a need, therefore, to develop such a technique that is both cost-effective and adaptable to one or more biologic structures to enable its widespread application.

SUMMARY OF THE INVENTION

The invention disclosed herein is a composition, method and use of a modified, bi-functionally-linked biopolymer, wherein the functional linkage is between a biomaterial surface and cells or biologic molecules.

The present invention takes advantage of molecular screening methods to prepare molecular structures with specific binding motifs and/or binding properties. These molecular structures are used as the polymer linkers. More importantly, the present invention allows for the self-selection and screening of molecular structures that display one or more specifically required properties. For example, one can select and prepare linkers that specifically bind with high affinity to one or more selected materials.

In one embodiment, the present invention uses peptide screening methods to prepare peptide binding motifs with specific binding properties, especially those with high affinity to one or more materials. More particularly, the present invention includes a bifunctional specificity structure, bifunctional peptide linker or peptide having a first and a second binding domain, wherein the first binding domain is selective for a first biomaterial and the second binding domain is selective for a second biomaterial. The first binding domain may binds specifically to a biopolymer and be selected from, e.g., the peptide amino acid sequences of SEQ. ID. NOS.: 1-22. The second binding domain may also be part of the same (e.g., a chimeric) or a different peptide that is attached to the first peptide having the first binding domain.

Examples of materials or biocompatible materials that may be bound by one or both of the domains of the bifunctional specificity structure, bifunctional peptide linker or peptides of the present invention include plastic, ceramic, metal, composites, polymers, and modifications and/or combinations thereof. Another example of a target for the present invention may be a biopolymer comprising one or more chloride doped polypyrrole subunits, poly-lactic acid based polymers, poly (lactic acid-co-glycolic acid) based polymers, magnetic materials, a biocompatible and/or biodegradable matrix, which may even be formed into a sheet. Yet another example is one or more growth factors, e.g., those biocompatible with nerve tissue.

In another embodiment of the present invention, synthetic polymers that exhibit tissue-specific properties are developed. The resulting "natural" polymer may then be used for biologic purposes such as in claudication, implantation, transplantation, biologic regeneration, growth, and as biologic replacements (valve, limb, etc).

In yet another embodiment, the surface of a synthetic polymer is modified using one or more screening method as presented above. For example, a random bacteriophage library that displays and expresses a peptide insert on one portion of the protein coat is used to prepare linkers that exhibit one or more of the properties required by one or more materials. Where synthetic polymers are used as the material, a peptide that specifically binds to one or more polymers is selected. Examples of polymers suitable for use with the present invention are oxidized polypyrrole doped with chlorine (PPyCl) and poly lactic acid-co-glycolic acid (PLGA).

In still another embodiment of the present invention, one or more bi-functionally linked polymers are synthesized such that one end of the linker (i.e., biologic molecule or structure) binds the polymer and the other end binds another biologic structure (e.g., nucleic acid, peptide, protein, chromophore, drug, growth factor, cell, chromophore, or other organic molecule). For example, the polymer may include one or more peptides with polymer binding domains on one end and a domain that binds to cells, drugs, or growth factors on the other end. Several biologic applications, as discussed above, are suitable for the bi-functionally linked polymers. Importantly, the physical properties of the polymer (or other material that may be used) are not altered. The bi-functionally linked polymer may be further shaped or modified for its use in various biologic applications, including claudication, implantation, transplantation, biologic regeneration, growth, and as a biologic replacement (valve, limb, etc). This type of surface modification method can be applied to a variety of synthetic material surface functionalization, and in-turn, selective surface reactivity.

A method of making the bivalent linker of the present invention includes the steps of selecting a peptide that includes a first binding domain peptide from a library of peptides that binds selectively to a biomaterial; and a second binding domain with the peptide that binds selectively to a target material. The peptide may have a length of about 7 to about 30 amino acids. The peptide may be bound and/or selected from a peptide phage display library and may include peptides selected from SEQ. ID NOS: 1-22.

The composition, methods and use of the present invention display clear advantages over current techniques used to develop biologic materials. Notable, the present invention does not require non-specific adsorption or covalent attachment methods. Furthermore, the present invention may be tailored to develop and prepare biologic materials that exhibit one or more desired properties.

In another embodiment, the present invention is a modified biologic material with a unique surface used to direct tissue regeneration. In one embodiment, the surface specifically presents biologic structures in a concentration-dependent fashion. Such a presentation when presented as a gradient may be used to guide cellular activity, growth, and/or regeneration in a time-dependent manner, e.g., akin to a nerve guidance channel. Notably, the present invention, when used, does not require multiple surgical procedures and reduces both the cost and surgical-related complications associated with tissue regeneration procedures.

In yet another embodiment, the present invention is for tissue engineering such that a hybrid or bi-functional biologic material is created. The bi-functional biologic material may present one or more biologic properties (i.e., through the linkage of biologic structures) at its surface in a specific or nonspecific pattern. The hybrid-biomaterial is designed to behave or exhibit properties similar to native tissue or a native organ. Applications of the hybrid or bi-functional biologic material include its use in tissue regeneration and/or as a bioreactor or biosensor, as well as targeted drug delivery.

The present invention provides a bifunctional specificity structure comprising: a peptide linker comprising a first binding domain and a second binding domain, wherein the first binding domain is selective for specific binding with high affinity to a first biomaterial which is an electrically conductive polymer or a biodegradable material, and the second binding domain is selective for specific binding with high affinity to a second biomaterial.

The present invention also provides a bifunctional peptide linker comprising: a first binding domain and a second binding domain, wherein the first binding domain is selective for a synthetic biocompatible polymer surface and the second binding domain is selective for a material.

BRIEF DESCRIPTION OF THE DRAWINGS

For more complete understanding of the features and advantages of the present invention, reference is now made to the detailed description of the invention along with the accompanying FIGURES.

FIG. 5 includes the peptide sequences from biopanning rounds 3 through 5 obtained from PPyCl-specific phage;

FIG. 6 depicts the predominant sequence for PPyCl as THRTSTLDYFVI (SEQ ID NO: 1), determined by comparing the percent amino acid occurrence per position for the 12 amino acid positions, where the maximum percent in each column corresponds to the highest amino acid occurrence for that position within the peptide;

FIG. 7 shows that the percent amino acid group per position for PPyCl gives a value that can be compared to the consensus sequence and the overall group occurrence (relative to the combinatorial library of peptides expressed on the pIII);

FIG. 12 shows that the predominant sequence for PLGA is SFPDTYVRVKPA (PLGA-1; SEQ ID NO.:7), as determined by comparing the percent amino acid occurrence per position for the 12 positions, wherein the maximum percent in each column corresponds to the greatest occurring amino acid for that position;

FIG. 13 shows that the percent amino acid group per position for PLGA-1 gives a value that can be compared to the consensus sequence and the overall amino acid group occurrence (relative to the combinatorial library of peptides expressed on the pIII);

FIG. 14 includes the peptide sequences from biopan rounds 3 through 5 obtained from PLGA-specific phage;

FIG. 15 shows that the predominant sequence for PLGA is KPLHSNKYYDRY (PLGA-2; SEQ ID NO.:15), as determine by comparing the percent amino acid occurrence per position for the 12 positions, wherein the maximum percent in each column corresponds to the greatest occurring amino acid for that position;

FIG. 16 shows that the percent amino acid group per position for PLGA-2 gives a value that can be compared to the consensus sequence and the overall percentage of amino acid group occurrence (relative to the combinatorial library of peptides expressed on the pIII);

DETAILED DESCRIPTION OF THE INVENTION

Figure 1:
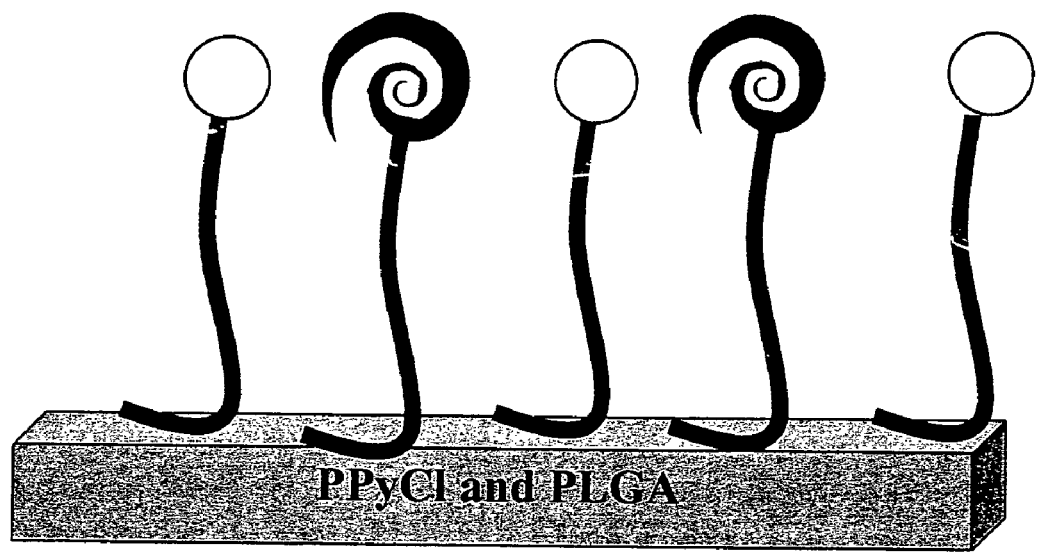
FIG. 1 is a microscopic illustration of a bi-functional linker connecting the material and biomolecules in accordance with the present invention.

While the making and using of various embodiments of the present invention are discussed in detail below, it should be appreciated that the present invention provides many applicable inventive concepts that may be embodied in a wide variety of specific contexts. The specific embodiment discussed herein are merely illustrative of specific ways to make and use the invention and do not delimit the scope of the invention. Various modifications and combinations of the illustrative embodiments, as well as other embodiments of the invention, will be apparent to persons skilled in the art upon reference to the description. It is therefore intended that the appended claims encompass any such modifications or embodiments.

All technical and scientific terms used herein have the same meaning as commonly understood by one of ordinary skill in the art to which this invention belongs, unless defined otherwise.

To facilitate the understanding of this invention, a number of terms are defined below. Terms defined herein have meanings as commonly understood by a person of ordinary skill in the areas relevant to the present invention. Terms such as "a," "an," and "the" are not intended to refer to only a singular entity, but include the general class of which a specific example is used for illustration. The terminology herein is used to describe specific embodiments of the invention, but their usage does not limit the invention, except as outlined in the claims.

The following are terms as they apply to this application. As used herein "material" is a substance with a surface that may come in contact with other materials and/or molecules. Materials may be microfabricated and may be made of a single compound, layered compounds, or a mixture of compounds of one or more molecules or chemicals such as polymers or polymer-blends, plastics, glass, metals, semiconductors, organic or inorganic compounds, and combinations, thereof. When the material is layered, the "surface" layer is one that will come in contact with one or more biologic structures.

As used herein, "biologic materials" also referred to as "biomaterials" are materials that exhibit, exert, or mimic biologic properties, such that they are able to bind, contact, react, combine, and/or interact in a manner that mimics, mirrors, or resembles cellular, prokaryotic, and eukaryotic biologic activity, process, reaction, interaction, or encounter. Biologic materials may include a material to which a biologic structure has been attached or to which a biologic structure is in contact with, wherein the contact is charged, covalent, polarizable, electrostatic interaction, fluxional, or through a molecular interaction such as hydrogen bonding.

"Biologic structures," as used herein, are structures that are of biologic origin, generally considered to be organic or carbon-containing compounds with functional groups such as amino, carboxyl, thiol or hydroxyl. Examples of biologic structures include nucleic acids, peptides, proteins, chromophores, cells, cytokines, cofactors, growth factors, tissues, organs, fatty acids, sugars, organic polymers and other simple or complex carbon-containing molecules, and combinations thereof. Biologic structures may be structures with a biologic backbone that also contain organic or inorganic modifications (e.g., modifications including but not limited to those that incorporate additional charge, structure, polarizability, hydrogen bonding, electrostatic interaction, and fluxionality to the biologic backbone). These biologic structures, also referred to as biomolecules, are complex molecules with some biologic activity and can include all of the examples used for biologic structures as well as other complex molecules such as drugs. For the present invention, the terms biomolecule and biologic structure are used interchangeably. Biologic structures may be produced, synthesized or engineered by biologic or nonbiologic processes. In one embodiment, biologic structures such as one or more host cells (e.g., tissue culture cells or clones, bacterial cells or bacteriophage) are used to express other biologic structures.

Figure 2:
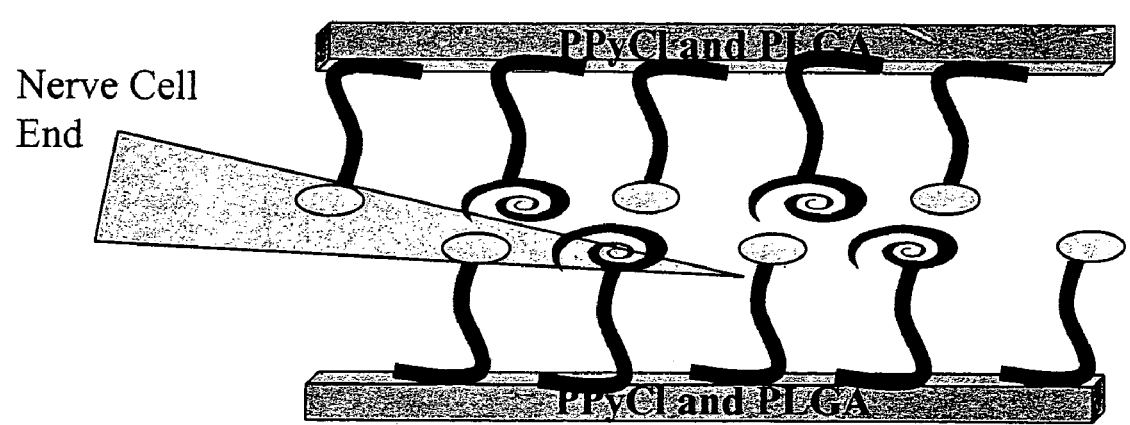
FIG. 2 is a microscopic illustration of a bi-functional system used inside a host.
Figure 3:
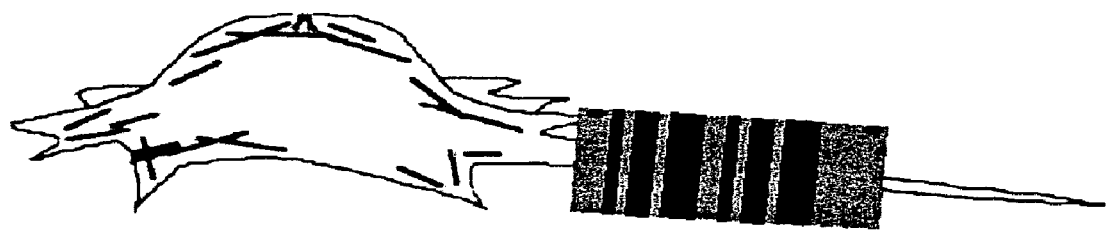
FIG. 3 is a macroscopic illustration of nerve cell axon being guided through the nerve guidance channel using a biomaterial with bi-functional linkers that contain biomolecules in a concentration gradient on the surface of the material in accordance with the present invention.

The present invention involves the development of unique and/or improved interactions between a first biologic structure, a material, and second biologic structure. FIGS. 1-3 demonstrate examples of these interactions shown at the microscopic and macroscopic level. Specifically, such interactions include a biologic "linker," as used herein to refer to a biologic structure that is able to contact a biomaterial and a second biologic structure to create a larger complex. The contact may be of any type that biologic structures encounter, such as covalent, electrical, electrostatic, hydrogen bonding, polar, magnetic, etc. FIG. 1 is an example of a linker that is a peptide and its interaction with a biomaterial on one end and one or more different biologic structures at the other end, where the biologic structures in this example are both biomolecules and cell.

The linkers used may be short or long biologic structures. They may be the native structure of ones that are synthesized, engineered or expressed in another biologic structure such as a cell. In one embodiment, the linkers are engineered and/or expressed by a different biologic structure. For example, bacteriophage can express or display biologic structures (e.g., or phage display) as a virus that is genetically engineered with one or more random biologic structures or molecules, such as a peptide or drug. In one case, the biologic molecule is a random peptide of a specified length expressed as a portion of the virus' exterior coat.

The advantage of using an expression system to obtain biologic structures is that large amounts of the biologic structures (e.g., libraries) are provided (i.e., displayed on the phage) enabling the rapid identification of structures that are specific to one or more materials and/or active in one or more particular biologic environments. Thus, specific biologic structures (e.g., peptides) that recognize one or more selected materials can be identified, a method akin to surface or material engineering. Furthermore, the material has become a biologic material (biomaterial) and, when a bi-functional biologic structure is used, one with the ability to contact another biologic structure or biologic material, then a bi-functional biomaterial is created as recognized by the present invention. Applications for bi-functional biomaterials include tissue engineering, tissue replacement, transplantation, biologic growth, differentiation or development, as examples. Further examples of compositions and methods of making bi-functional biomaterials of the present invention are presented below.

Using Phage Display to Identifying Material-Specific Biologic Structures.

Figure 4:
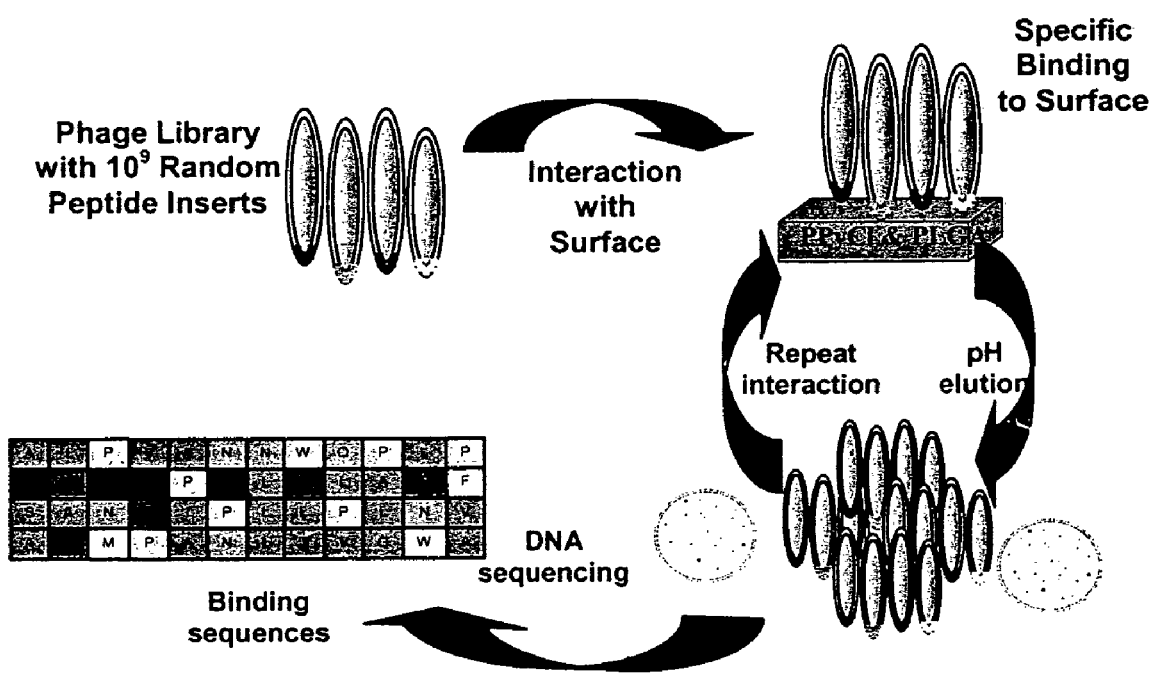
FIG. 4 is an illustration of the screening (biopanning) process used for selecting one or more peptides that recognize the surface of a material. The binding sequence peptides are shown in SEQ ID NOS 25-28, respectively, in order of appearance.

A filamentous virus (i.e., bacteriophage) may be used to produce large amounts of one or more biologic structures. Commercially-available libraries that contain random assortments of biologic structures with certain qualities (e.g., length, innate structure, species) may be used. For example, bacteriophage libraries (also referred to herein, as phage libraries) have been developed that include an assortment of biologic structures such as peptides of specific lengths (e.g., 12 amino acid linear, 7 amino acid linear, or 7 amino acid constrained where cysteines are at the $1^{st}$ and $9^{th}$ position on the peptide to create a loop by the disulfide linkage between the two cysteines) on the minor coat protein (pIII) of the M13 coliphage. Another benefit of using a large library such as this is that after finding that one or more specific biologic structures (e.g., peptides) that can contact or bind a selected material, the library can be used to find the specific amino acids involved in contacting or binding to the material. An example of the process used to find specific biologic structures and/or characteristics about them, also referred to as a screening method, is shown in FIG. 4. Phage display libraries and experimental methods for using them in biopanning are further described, for example, in the following U.S. patent publications to Belcher et al.: (1) "Biological Control of Nanoparticle Nucleation, Shape, and Crystal Phase"; 2003/0068900 published Apr. 10, 2003; (2) "Nanoscale Ordering of Hybrid Materials Using Genetically Engineered Mesoscale Virus"; 2003/0073104 published Apr. 17, 2003; (3) "Biological Control of Nanoparticles"; 2003/0113714 published Jun. 19, 2003; and (4) "Molecular Recognition of Materials"; 2003/0148380 published Aug. 7, 2003.

The present invention was exemplified by a series of working examples. In one embodiment of the present invention, a Ph.D.-12™ Phage Display Peptide Library Kit (New England Biolabs, Beverly, Mass.) was used to screen biologic structures (e.g., peptides). The kit contains a library with approximately $10^9$ different 12-amino acid linear peptide inserts fused to the pIII coat protein of M13 coliphage. An initial volume of 1 μL of the phage-display library (in solution and corresponding to a $1 \times 10^{12}$ phage/μL) was used to begin screening against one or more materials, a process referred herein as biopanning. Biopanning took place in 1 mL of Tris-buffered saline (TBS) containing 0.1% (vol/vol) Tween-20 (0.1% TBS-T); each material was incubated with the library for at least about 1 hour at room temperature. Materials were then washed (several times) with 1 mL of 0.1% TBS-T to discard non-specific phage. To disrupt any phage binding that was not specific to the surface of the material, 500 μL of glycine-HCl (pH 2) was added to the above mixture for at least about 9 minutes at room temperature. The solution was then collected and brought to a neutral pH with Tris-HCl (pH 9). Half of the volume of the solution was then introduced (at a 1:100 dilution with growth media) to *Escherichia coli* (*E. coli*) ER2837 bacteria (New England Biolabs, Beverly, Mass.) that had been cultured at least about overnight.

The phage-bacterial solution was incubated at least about 5 hours in a shaker at 37 degrees Centigrade (allows virus to infect bacteria). Bacteria were collected by centrifugation (at least about 14,000 rpm for 10 minutes) and phage were precipitated with poly(ethylene glycol) or PEG for at least about 15 minutes at a refrigerated temperature (4 degrees Centigrade). A second centrifugation (at least about 10,000 rpm for 15 minutes) followed and the pellet was resuspended in 200 μL of TBS. Meanwhile, the concentration of phage was also calculated (generally from a sample of phage-bacterial solution and/or from a sample of the phage solution when incubating with the material). The techniques used are those well known to one of ordinary skill in the art of molecular biology and includes plating the phage or allowing a various concentrations of phage solutions to infect a known amount of bacteria. When using the infection technique, bacteria with lacZ gene may be used and plated in the presence and absence of isopropylthio-β-D-galactoside (IPTG) and 5-Bromo-4-chloro-3-hydroxyindolyl-β-D-galactose (X-gal) for visual determination of bacterial growth on "titer plates." The phage concentration may then be determined by the following:

$$\text{Concentration of phage from titer plate (pfu/μL)} \times (1\ \mu L/1E^{-6}L) \times (5\ \text{copies of pIII/1 pfu}) \times (1\ \text{mole}/6.023 \times 10^{23}\ \text{molecules}) \quad (1)$$

where, pfu=plaque forming unit.

Hi-Throughput Screening of Material-Specific Biologic Structures.

Several biopanning rounds are generally used to determine material-specific biologic structures and their material-specific contact or binding regions. For each biopanning round, the phage concentration is used to determine the amount (as volume) used in the next round of biopanning against the material. A fresh piece of material was used for the next screening, where the phage amount was at least about $10^9$ pfu. Multiple rounds of biopanning follow, generally at least about five rounds to determine the consensus sequence involved in binding the material.

From the $3^{rd}$ to the $5^{th}$ round of biopanning, blue plaques were picked and each amplified separately, 1:100 in growth media with an overnight culture of *E. Coli* and allowed to grow (e.g., amplify) for 5 hours. Bacteria were then separated by centrifugation for 30 seconds and 500 μL of the phage solution was precipitated for 10 minutes at room temperature with PEG, followed by centrifugation for 10 minutes to pellet the phage. The pellet was suspended in a solution of NaI (ruptures the phage protein coat) and ethanol (approximately 250 μL) was used to precipitate DNA from the phage. Precipitated DNA was suspended in at least about 60 μL chemical-free, filtered water and the nucleotide sequences obtained and translated into peptide sequences (N-terminus to C-terminus) as shown in FIG. 4. Non-genetically engineered phage (e.g., naturally occurring or wild type [WT]) lacking a peptide insert on the pIII protein coat will appear as clear plaques during biopanning (i.e., when plated on titer plates in the presence of IPTG and X-gal).

Following the above method and after several rounds of screening or biopanning, a consensus region of the biologic structures (e.g., consensus peptide or amino acid sequences) will be found and will represent the preferred or common regions involved in contacting or binding of the material. For rapid analysis, several steps of the above method may be automated and without undue experimentation, as is well-known to one of ordinary skill in the art of molecular biology.

Examples of Materials for Developing Bi-Functional Biomaterials.

In general, ideal materials for the present invention are those that may contact a biologic structure and form an interaction that is more than a non-specific interaction—a interaction well-known to one of ordinary skill in the art of physiology. Examples of materials for the present invention include plastic, ceramic, metal, other composites, polymers, and modifications and/or combinations thereof. The material may be one that is shaped, blended, or deposited onto another surface.

A preferred embodiment of the invention comprises use of electrically conductive polymers including synthetic electrically conducting polymers in biopanning experiments. Electrically conductive polymers are known in the art of nerve regeneration: (1) U.S. Pat. No. 5,843,741 to Wong et al. (Dec. 1, 1998) "Method for Altering the Differentiation of Anchorage Dependent Cells on an Electrically Conductive Polymer"; (2) U.S. Pat. No. 6,095,148 to Shastri et al. (Aug. 1, 2000) "Neuronal Stimulation using Electrically Conductive Polymers". For example, the polymer can comprise a conjugated polymer backbone, resulting in electron delocalization and low energy optical transitions, and these types of polymers are known in the art as conducting polymers. Conducting polymers are an important class of materials because of their potential applications in electrical, optical, and sensing devices, as well as biological and biomedical applications. Prototypical electronic conducting polymers include polyacetylene, polydiacetylene, poly(phenylene vinylene) (PPV), poly-para-phenylene, polypyrrole, polyaniline, polythiophene, and the like. Doping can be used for conducting polymers such as polyaniline and polypyrrole to improve their conductivities, as well as their solubilities in water. Self-doped sulfonated polyaniline (SPAN) and doped polypyrrole (PPy), for example, have charged backbones and have high solubilities in water. PPV can be made with use of water-soluble precursors as well which can be used with doping agents.

Patent literature which describes a variety of conducting and semiconducting polymers includes: (a) U.S. Pat. No. 4,929,389 to Aldissi ("Water-Soluble Conductive Polymers"); (b) U.S. Pat. Nos. 5,294,372 and 5,401,537 to Kochem et al. ("Aqueous Dispersions of Intrinsically Electroconductive Polyalkoxythiophenes, a Process for their Preparation and their Use"); (c) U.S. Pat. No. 5,670,607 to Chen ("Miscible Forms of Electrically Conductive Polyaniline"); (d) U.S. Pat. No. 5,569,798 to Wudl et al. ("Self-Doped Polymers"); (e) U.S. Pat. Nos. 5,648,453 and 5,688,873 to Saida et al. ("Electroconductive Polymer and Process for Producing the Polymer"); (f) U.S. Pat. No. 5,968,417 to Viswanathan ("Conducting Compositions of Matter"); and (g) U.S. Pat. No. 6,534,329 to Heeger et al. ("Visible Light Emitting Diodes Fabricated from Soluble Semiconductor Polymers"), and are each hereby incorporated by reference for their entire teachings including synthesis and characterization. These patents, for example, describe covalently linking Bronsted acid groups to polymer backbones, zwitterionic structures, self-doping, doping with acceptors and donors which oxidize or reduce the polymer chain, cycling between neutral and ionic states, stability, and pi-conjugation of electronic systems which provides semiconducting or conducting behavior. In addition, the many applications of conducting polymers are described.

Electrically conductive polymers are also described in, for example, Concise Encyclopedia of Polymer Science, J. I. Kroschwitz, Ex. Ed., John Wiley, 1990, pages 298-300, which is hereby incorporated by reference. The polymers are described as having conjugated pi-electron backbones which can provide properties such as, for example, low energy optical transitions, low ionization potentials, and high electron affinities. They can be oxidized or reduced more readily than conventional polymers. Doping of the following types of conductive polymers is described: polyacetylene, poly(p-phenylene), poly(p-phenylene sulfide), polypyrrole, and polythiophene.

Additional conducting polymers and their use in patterning on various substrates is described in U.S. Pat. No. 5,976,284 to Calvert et al. ("Patterning Conducting Polymer Surfaces and Process for Preparing the Same and Devices Containing the Same"). This '284 patent teaches that, in principle, any polymer having an electrical conductivity of at least sigma$>10^{-3}$ S/cm, preferably at least sigma$>10^{-1}$ S/cm, can be used as the conducting polymer. Also, conducting polymers are described in Chapter 11 of Organic Conductors, J. P. Farger, Ed. Marcel Dekker, NY, N.Y., 1994, which is incorporated herein by reference. Conducting polymers include, e.g., cis and trans polyacetylenes (PA), polydiacetylenes (PDA), polyparaphenylenes (PPP), polypyrroles (PPy), polythiophenes (PT), polybithiophenes, polyisothianaphthene, polyphenylenevinylenes (PPV), polythienylvinylenes (PTV), polyphenylenesulfide (PPS), and polyaniline (PAni), and the structures of these polymers are shown in the '284 patent. In these structures, it is to be understood that H atoms may be replaced by substituents, such as $C_{1-18}$-alkyl, or phenyl or groups containing ionic groups such as carboxylate or sulfonate. These groups may be attached directly or through ester, ether, or amide links. In general, substitution worsens the electrical conductivity of the conducting polymer, but may enhance features such as solubility or orientation at the air/water interface, for example. Other references which further describe the synthesis and properties of these conducting polymers include: M. F. Combarel et al, C. R. Acad. Sci. Ser. C, vol. 262, p. 459 (1966); L. T. Yu et al, J. Polym. Sci. Symp. C, vol. 16, p. 2931 (1967); M. Doriomedoffet al, J. Chim. Phys. (Paris), vol. 68, p. 39 (1971); T. Ito et al, J. Polym. Sci. Chem. Ed., vol. 12, p. 11 (1974); H. Shirakawa et al, Chem. Commun., p. 578 (1977); C. K. Chiang et al, Phys. Rev. Lett., vol. 39, p. 1098 (1977); P. J. Nigrey et al, Chem. Commun., p. 594 (1979); A. G. MacDiannid et al, Synth. Metals, vol. 1, p. 101 (1980); D. M. Ivory et al, J. Chem. Phys., vol. 71, p. 1506 (1979); A. F. Diaz et al, Chem. Commun., p. 635 (1979); K. K. Kanazawa et al, Chem. Commun., p. 854 (1979); G. Tourillon et al, J. Electroanal. Chem., vol. 135, p. 173 (1982); E. M. Genies et al, Synth. Metals, vol. 36, p. 139 (1990); H. W. Gibson et al, J. Am. Chem. Soc., vol. 105, p. 4417 (1983); M. C. Dos Santos et al, Phys. Rev. Lett., vol. 62, p. 2499 (1989); Synth. Metals, vol. 29, p. E321 (1989); H. Kiess, ed., Conjugated Conducting Polymers, Springer Series in Solid State Sciences, Vol. 102, Springer-Verlag, Berlin, 1992.

For example, chlorine doped polypyrrole (PPyCl) is an electrically conductive material; an oxidized version of polypyrrole has been used as a substrate for nerve regeneration. The advantage of this type of material is that it can be electropolymerized to form sheets or other shapes of interest.

Materials may also be those that are biodegradable. For example, poly (lactic acid-co-glycolic acid) (PLGA) is easy to prepare, its surface area can by controlled as well as its degradation rate. See, e.g. *Sustained and Controlled Release Drug Delivery Systems*, Ed. J. R. Robinson, 1978 including discussion at page 328, incorporated herein by reference in its entirety.

Electropolymerization of Polypyrrole

Polypyrrole was oxidized enabling current to pass through. The addition of chloride as radical anions or "dopants" provide charge neutrality along the highly conjugated backbone. In one embodiment of the present invention, a PPyCl film is electrochemically deposited on indium tin oxide (ITO)-conductive borosilicate glass (Delta Technologies, Still Water, Minn.). The ITO glass, shaped as slides, may be cleaned before use by sonication in hexane, methanol, and dichloromethane, 5 minutes each.

Electrochemical deposition of PPyCL was made with a three-electrode setup consisting of a saturated calomel reference electrode, platinum gauze counter electrode, and an ITO slide as the working electrode. The polymer was deposited at a constant potential of 720 mV (versus the saturated calomel reference) from an aqueous solution of 0.1 M pyrrole monomer (Fisher, Scientific, Palatine, Ill.) containing 0.1 M NaCl (Fisher, Scientific, Palatine, Ill.) as the dopant. A Pine Instruments AFRDE5 bipotentiostat was used as the DC voltage source. Film thickness ranged from 30-40 μm as determined by integrating current over time. The thickness was controlled by the passage of charge based on the standard value of 50 mC/cm$^2$. The charge passing through the working electrode was measured with a current integrator (IT001, Cypress Systems, Inc.) coupled to a multimeter (Sperry, DM-8A) for digital display. Films were rinsed with sterile water and dried in a desiccator for at least about two days before use.

Material-Specific Biologic Structures: Selection Against a Material

Biologic structures that select for a specific material may be further analyzed to determine how or where the contact to the material occurs. In one embodiment, biologic structures such as peptides are sequenced to determine consensus binding regions. The biologic structures may be obtained after rounds of biopanning or through other methods of attachment in which nonspecific interactions are eliminated (e.g., material is washed to remove unbound biologic structures such as peptides). The methods are well known to one of ordinary skill in the art of molecular biology.

In one embodiment, phage expressed peptides were allowed to bind to PPyCl and plaques grown after biopan rounds 3 through 5 were sequenced. Results of the sequencing (using one-letter amino acid abbreviations) are shown in FIG. 5 in which a predominant sequence (SEQ ID NO.:1) was found; however additional statistical analysis should be performed in order to verify that it is a consensus binding region. In one embodiment of the present invention, functional group reactivity is performed, where amino acid side chains are grouped together, i.e., basic, acidic, hydrophobic, hydroxyl, aromatic, amide, methionine, and proline (one or more amino acids, such as cysteine, may left out when there is a lack of occurrence in the sequenced samples). The analysis shows the types of biologic structure (peptide)—biologic structure (peptide) interactions as well as biologic structure (peptide)—material interactions that occur.

FIG. 6 shows an example of the statistical analysis in which the percent amino acid group per position is displayed. For example, in FIG. 6, hydroxyl amino acid groups appear two time more often as compared to their presence in the parent combinatorial peptide library. The consensus region is represented in the last line of the FIG. 6 as THRTSTLDYFVI (SEQ ID NO.:1). Additionally, the consensus binding region was analyzed for amino acid functional group reactivity (FIG. 7) and helps to illustrate possible interactions between functional groups and the material (i.e., between the biologic structure and the surface of the material).

Material-Specific Biologic Structures: Verification of Specificity

Some biologic structures, especially those produced in large amounts through the help of another biologic structures (e.g., expressed through host cells such as bacteria or bacteriophage), may contain consensus regions that are not only the result of interactions between the material but are consensus regions based on the expression system or method use to produce the biologic structure. In one embodiment of the present invention, the biologic structure consensus region is verified, especially that it is not a consensus region resulting from cell growth during biopanning (e.g., amplification). For example, if a modified host multiplies better than a naturally occurring host, then there is a possibility that the modified host containing the consensus region was selected because of its ability to grow, not because of material-specific interaction.

Verification includes expressing the specific consensus region (or entire biologic structure containing the consensus region) in the host, growing the host and comparing the number grown to that obtain from a non-modified host. For example, in one embodiment, a peptide containing the material consensus region for interacting with PPyCl was displayed on phage and amplified as previously described. Titer counts of these phage were compared to the amplification of random phage and WT (those not allowed to interact with or raised against PPyCl) as shown in FIG. 8.

Figure 8:
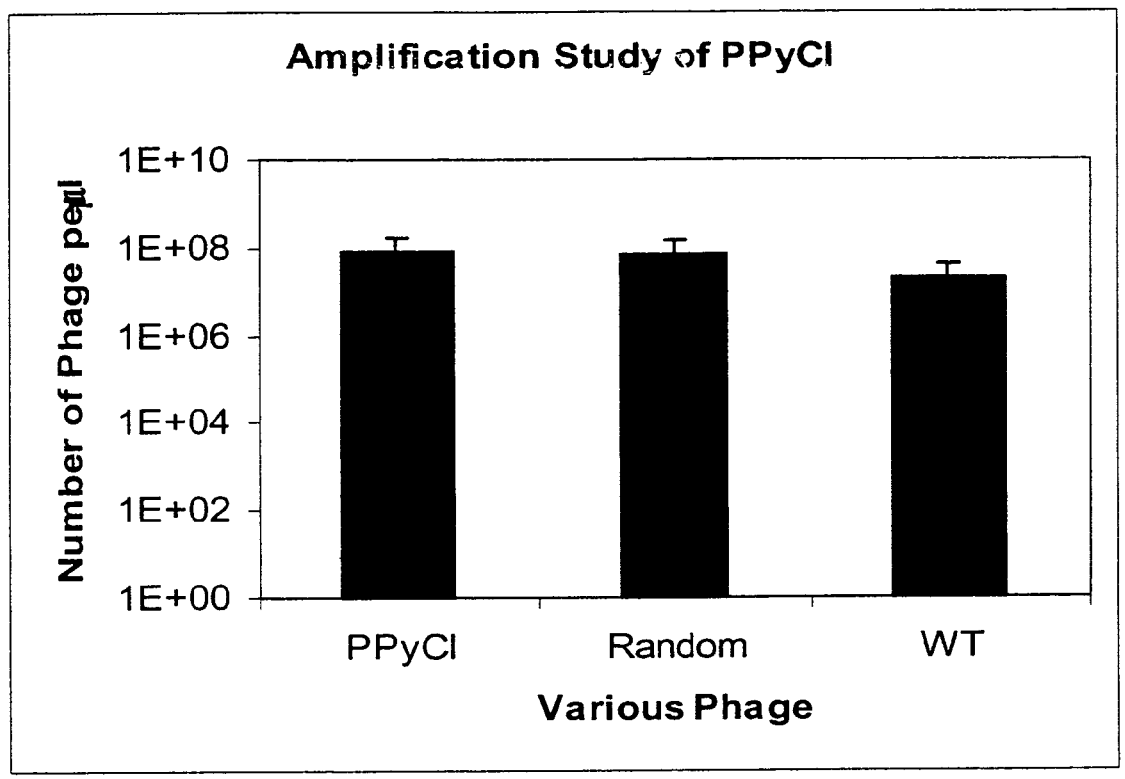
FIG. 8 is an example of an amplification study of phage selected for PpyCl, where the PPyCl sequence is THRTSTLDYFVI (SEQ ID NO.:1) and the random sequence is IEHPKTPDSHSR (SEQ ID NO.:4)

FIG. 8 shows that PPyCl-specific phage (PPyCl bar) amplified to an average count of 8±2 during a $10^{-7}$ dilution, at a concentration of $8\pm2\times10^7$ pfu/µL, or 0.66±0.05 nM, as obtained from equation (1). The randomly selected engineered phage amplified to an average phage count of 7±2 during a $10^{-7}$ dilution, at a concentration of 0.58±0.05 nM. WT phage amplied to an average phage count of 2±2 during a $10^{-7}$ dilution or a concentration of 0.17±0.05 nM. Because the growth pattern was similar for each group analyzed, PPyCl-specific phage are found to express a PPyCl-specific consensus region and not a growth or expression-related consensus region.

Determining the Biologic Structure-Material Interaction

The consensus region of the biologic structure is presumed to undergo a type of specific interaction with the material. The interaction may be any of the interactions previously described (e.g., covalent, electrical, electrostatic, hydrogen bonding, polar, magnetic, etc., as examples). Several methods are available to determine the type of interaction that occurs between the biologic structure and the material and to determine that the interaction is specific. Methods are those readily apparent to one of ordinary skill in the art of molecular biology and some examples are discussed below.

Figure 9:
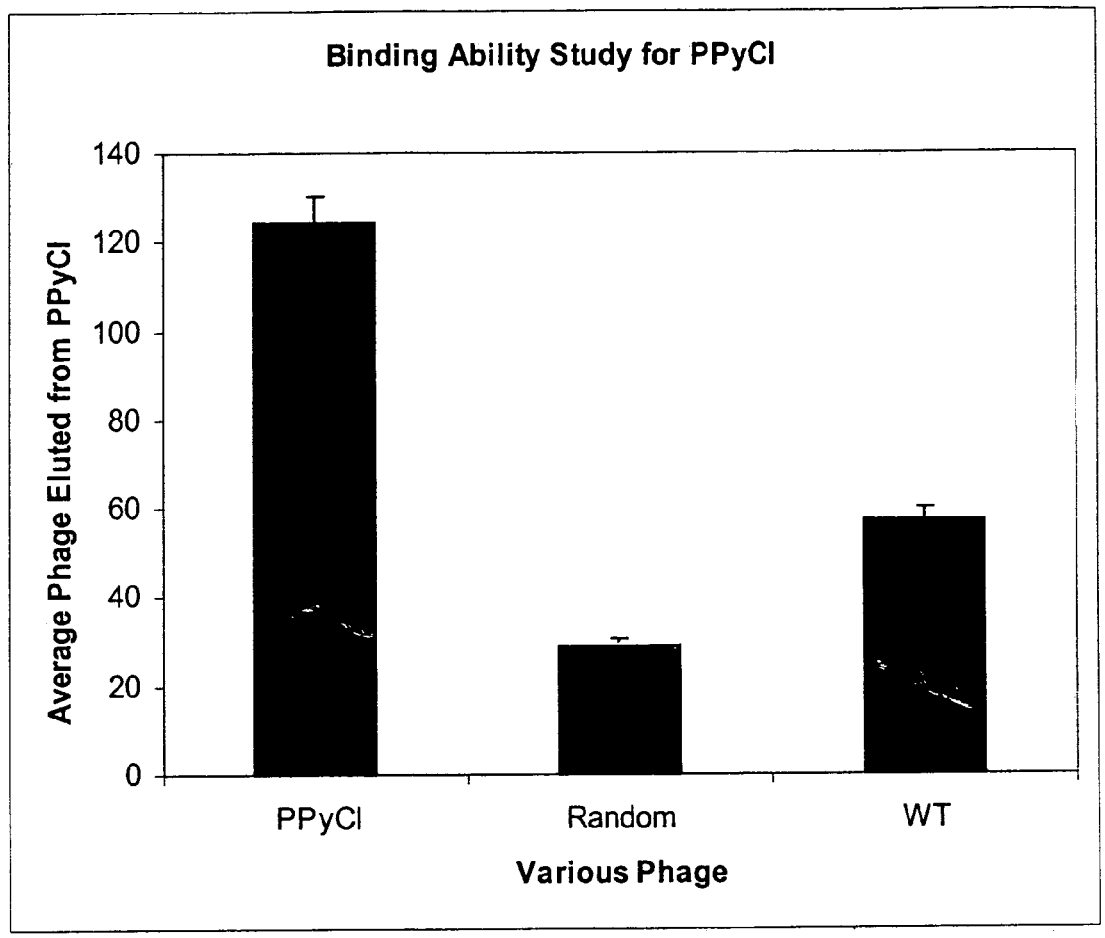
FIG. 9 is an example of a binding affinity study of phage selected for PPyCl., where PPyCl sequence is THRTSTLDYFVI (SEQ ID NO.:1) and the random sequence is IEHPKTPDSHSR (SEQ ID NO.:4)

Titer counts. The use of titer count as a binding study for the peptide on PPyCl is semi-quantitative and provides a relative binding comparison of phage counts per PPyCl-specific phage, randomly selected engineered phage or WT phage. Initial amounts of $1\times10^8$ pfu phage interacted with the PPyCl. PPyCl samples were then washed at least about three times with 1 mL of 0.1% TBS-T to remove unbound phage. Elution of bound phage with 500 µL Glycine-HCl (pH 2.2) for 9 minutes was used to disrupt phage bound to the surface. Titer counts were obtained from consensus peptide phage experiments and compared to titer counts of WT and random peptide phage (and used to compare the binding ability of PPyCl-specific phage, randomly selected engineered phage, and WT by comparing the amount of phage that could be eluted off the surface of PPyCl). Using 500 µL of glycine-HCl (pH 2.2), the titer count method showed that PPyCl-specific phage bind more successfully than the other phage (FIG. 9). Random selected engineered phage had the lowest recovery with an average count of 29 phage. WT had an average recovery of 57 counts. PPyCl-specific phage had a recovery rate (phage bound to the surface) of 124 counts.

Figure 10:
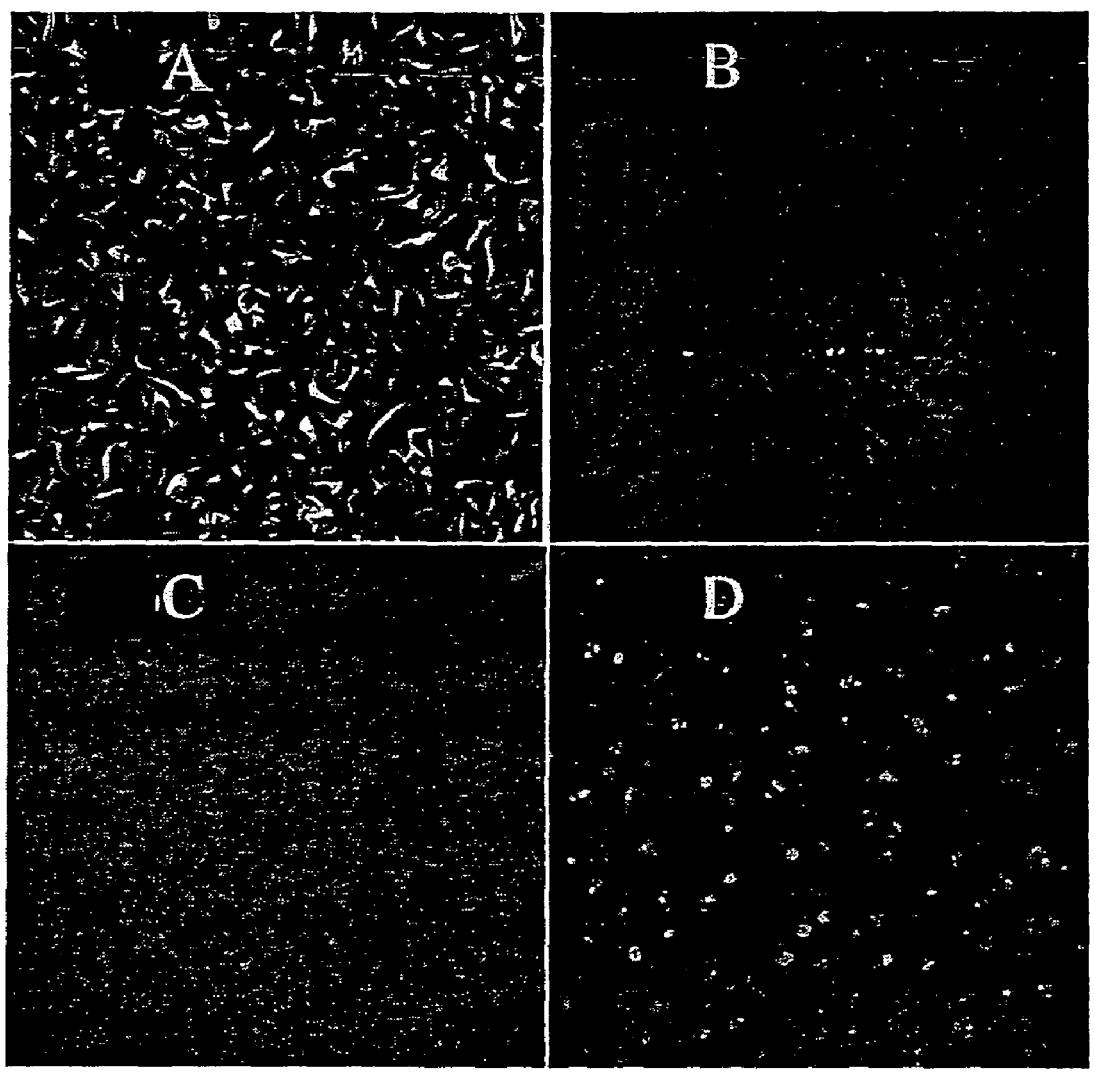
FIG. 10 are reflectance image of (A) PPyCl with phage, (B) PPyCl-specific phage at 1°-2°, (C) random phage at 1°-2°, (D) WT at 1°-2°, (E) 1°-2°, (F) 2°, and (G) mounting media, wherein PPyCl sequence is THRTSTLDYFVI (SEQ ID NO.:1) and the random sequence is IEHPKTPDSHSR (SEQ ID NO.:4)

Immunochemistry. With the immunochemistry technique, fluorescently-labeled phage bound to the surface of PPyCl are visualized microscopically and enables the number of—material bound phage to be quantified. A biotinylated antibody to the M13 bacteriophage specific to pVIII (Anti-fd Bacteriophage-Biotin Conjugate from rabbit, Sigma-Aldrich Corp., St. Louis, Mo.) and the biotin-streptavidin interaction were used to attach fluorescein-labeled-streptavidin (Exaplha, Boston, Mass.) to phage. Phage were visualized on the material using fluorescence microscopy. Phage were at a concentration of $1\times10^4$ pfu/PL and allowed to interact with 1 cm×0.5 cm sample of PPyCl for at least about 1 hour. The material (PPyCL) was then washed at least about three times with 1 mL of 0.1% TBS-T to remove unbound phage from the material. A primary anti-body (1°), at a dilution of 1:400 (antibody:4% Bovine Serum Albumin [BSA] in TBS at pH 7.5) was added to the material for at least about 1 hr at room temperature. Samples were washed at least about two times with 1 mL of TBS (pH 7.5). A secondary antibody (2°) of fluorescein-labeled-streptavidin at a dilution of 1:200 (fluorescein-labeled—streptavidin: 4% BSA in TBS at pH 7.5) was added to the material for at least about 30 minutes at room temperature in the dark. Material was then washed at least about two times with 1 mL of TBS (pH 7.5) and visualized after mounting on microscope slides. The images are shown in FIG. 10 using a Leica TCS 4D confocal microscope equipped with differential interference contrast optics and a Kr/Ar mixed gas laser with a selected excitation wavelength of 488 nm (for fluoroscein) and emission was collected through a 40× oil immersion objective (Microscopy Laboratory of the Institute for Cellular and Molecular Biology, University of Texas, Austin, Tex.).

From FIG. 10B, PPyCl-phage are shown to have specific interaction with the PPyCl surface. FIGS. 10B-G show the high intensity fluorescence that is the PPyCl-specific interaction (with little random binding). Random phage and WT were used to verify that the peptide sequence on PPyCl-specific phage was specific to PPyCl. The peptide sequence that was expressed on the random phage was different than that of the peptide sequence displayed on PPyCl-phage, and also has lower intensity, suggesting that the PPyCl-specific phage bind specifically to PpyCl, while the random phage has no specific interaction. For example, comparison of FIG. 10B (PPyCl-specific phage) and FIG. 10D (WT) that the interaction is specific (e.g., higher intensity of fluorescence with PPyCl-specific peptides). FIGS. 10E-G show that the amount of fluorescence from the antibody, fluoroscein-labeled-streptavidin, and mounting media is minimal compared to the intensity of labeled phage. All samples were imaged using the same intensity of laser light and exposure times, except for the reflectance image (FIG. 10A) which was not imaged with the laser but with a 100 W Hg lamp.

The present invention demonstrates that the surface of a material may be modified to encourage an interaction with a biologic structure and can be used to create a bi-functional biomaterial. From the methods such as those using immunochemistry, the interaction between material and biologic structure is found to be specific. In one embodiment, a peptide sequence of THRTSTLDYFVI (SEQ ID NO: 1) is the consensus region that specifically interacts with the material, PPyCl. Further embodiments include spatially controlling the concentration of biologic structure on the material surface and including one or more biologic structures as linkers. For example, when used with neural tissue, a biomaterial of the present invention can include biologic structures such as neural cells and neural-specific biomolecules such as nerve growth factor or other neural-acting agents or drugs. The present invention will further expand the possibilities of the tissue engineering industry. In yet another embodiment of the present invention, the material is one that can be modified over time (either synthetically or naturally) such as those that are biodegradable. Additional working examples are presented below.

Example Using a Biodegradable Material

Some materials may be controlled, such as their rate of degradation, immunogenic response, etc., and may, thus serve as improved bi-functional biomaterials. Controlling the rate of degradation enables one to engineer suitable biomaterials for tissue-related applications. In one embodiment of the present invention, a material, such a biodegradable PLGA is cast in a form. Casting methods that are used are those readily apparent to one of ordinary skill in the art of polymer chemistry. In one example, the material is solvent cast. In another embodiment, the material is cast into a film that may be at least about 80-150 μm thick with a smooth surface.

PLGA is generally used in an 85:15 percent ratio (lactic acid:glycolic acid) or PLGA (85:15). The PLGA film is constructed by adding 1 mL dichloromethane (Fisher Scientific, Palatine, Ill.) to 100 mg PLGA (Polysciences Inc., Warrington, Pa.) to yield a 100 mg/mL concentration. The mixture is stirred to homogeneity and dried overnight in a Pyrex™ 100 mL glass beaker for solvent evaporation. Film thicknesses of at least about 150-80 μm were determined by the relative concentrations of PLGA and solvent, such as dichloromethane. PLGA films may be stored in a UV-protected desiccant for at least about 1 month. Many forms of PLGA undergo hydrolysis of the ester bonds or oxidize over time.

PLGA is a material that is biologically compatible; however, it does not have the ability to interact specifically with one or more select biologic structures. The present invention presents methods to identify biologic structures that are specific to PLGA.

Biologic Structures Specific for Degradable Materials

Figure 11:
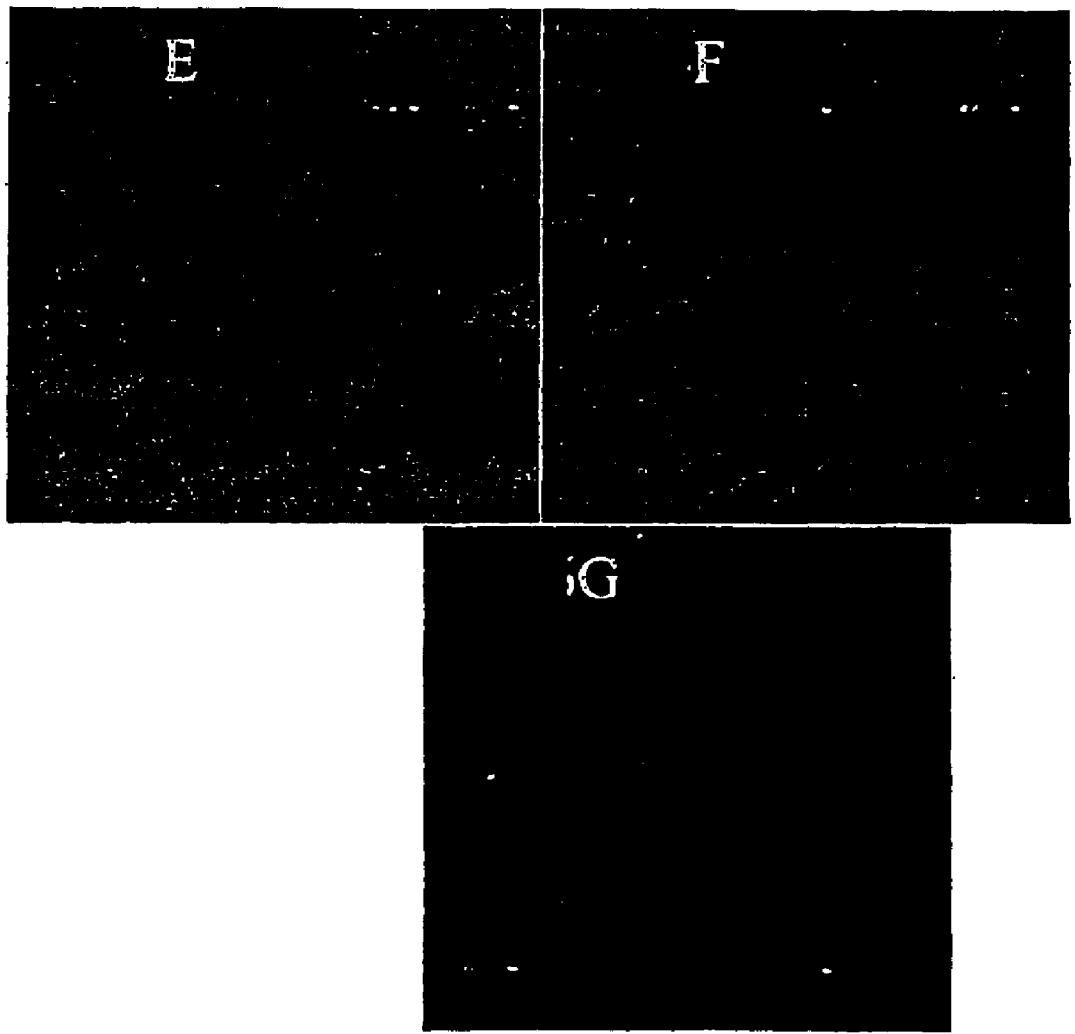
FIG. 11 includes peptide sequences from biopan rounds 2 through 4 obtained from PLGA-specific phage in accordance with the present invention.

Biologic structures such as peptides that were specific to PLGA were obtained from the phage selected after the $2^{nd}$ or later biopanning rounds. Results of peptide sequences obtained from biopanning rounds 2 through 4 are illustrated in FIG. 11.

More thorough analysis was performed on the peptide sequences obtained from the first screening of PLGA or PLGA-1 (FIG. 12). The percent of the amino acid groups per position was determined and compared with the consensus sequence and the percent occurrence of the amino acid group in the combinatorial library of peptides (FIG. 13). The consensus regions as shown in FIG. 12 for PLGA-1 is SFPDTYVRVKPA (SEQ ID NO.:7).

The percent amino acid group per position gives a relatively good confirmation of the consensus sequence, but it does not predict the consensus sequence completely. For example, the $4^{th}$ position has relatively high values for amino acids that act as Lewis-bases and amino acids that contain a hydrophobic reactive group that seem to compete for the $4^{th}$ position with acidic reactive groups. This is also the case for the $8^{th}$ position with high values for hydrophobic and hydroxyl reactive groups that do not match the basic reactive group in the consensus sequence. We were also interested in the regions of hydroxyl reactive groups in the beginning of the sequence and hydrophobic reactive groups at the end of the sequence of the peptide. This is consistent with common protein structure with the hydrophobic section of the peptide coiled in the interior of the tertiary peptide structure and the hydroxyl section on the exterior of the peptide in aqueous solution. A more thorough analysis is needed to determine the binding of the peptide to the surface of the PLGA and eventually determining what role, if any, the hydroxyl and hydrophobic amino acids have in the binding of the peptide to PLGA.

A second peptide screening was performed on PLGA to determine similarities in peptide sequences. The second screening of PLGA with the 12-mer library of peptides was conducted for PLGA-2 (using a similar method as for the screening of PLGA-1 with the 12-mer library of peptides). The results from the second screening for PLGA are shown in FIG. 14. With this second screening of PLGA, the percent of the amino acid groups per position was determined and compared with the consensus sequence and the percent occurrence of the amino acid group in the combinatorial library of peptides (FIGS. 15 and 16). The consensus regions as shown in FIG. 15 for PLGA-2 is KPLHSNKYYDRY (SEQ ID NO.: 15).

The sequences obtained for PLGA-1 (SFPDTYVRVKPA) (SEQ ID NO: 7) and PLGA-2 (KPLHSNKYYDRY) (SEQ ID NO: 15) show similarities such as the hydroxyl reactive groups localized on one end and the single aspartic acid in the peptide.

Verification that One ore More Biologic Structures are Specific to a Biodegradable Material The material-specific phage were further analyzed to verify that the consensus regions for PLGA-1 and PLGA-2 were specific to the material and not to host variables such as growth or biopanning. PLGA-1 and PLGA-2 were compared to the random and WT phage.

Figure 17:
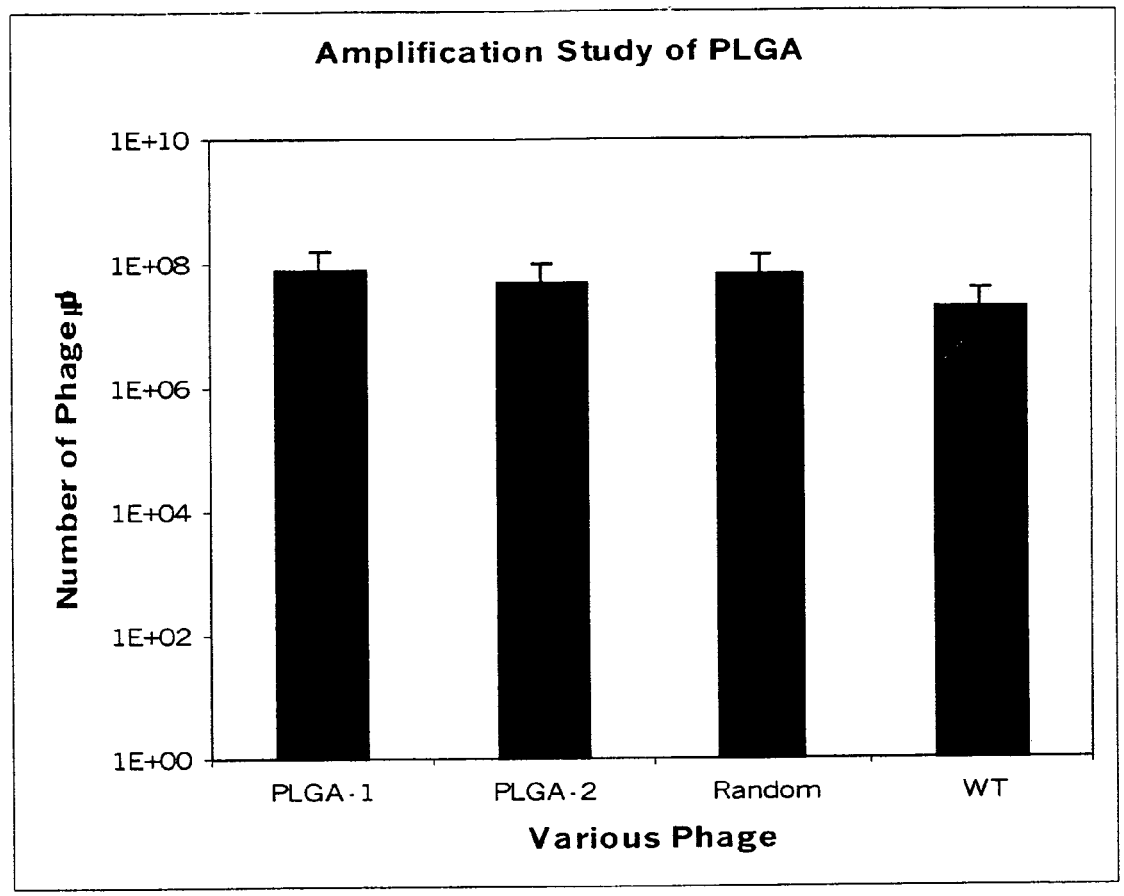
FIG. 17 is an example of an amplification study of phage selected for PLGA, where the PLGA-1 sequence is SFPDTYVRVKPA (SEQ ID NO.:7), the PLGA-2 sequence is KPLHSNKYYDRY (SEQ ID NO.:15), and the random sequence is IEHPKTPDSHSR (SEQ ID NO.:4)

The amplification study for PLGA shows that the PLGA-1 and PLGA-2—specific phage were able to amplify to the same level as the random-phage library or WT (FIG. 17) and were, thus, specific interactions. FIG. 17 shows that PLGA-1 phage amplifies the most with the average phage count of 8±2 during a $10^{-7}$ dilution, denoting a concentration of 0.66±0.05 nM. PLGA-1 and PLGA-2 counts are almost identical; 5±2 during a $10^{-7}$ dilution for PLGA-2 (a concentration of 0.42±0.05 nM). Random phage amplified to a count of 7±2 during a $10^{-7}$ dilution (at concentration of 0.58±0.05 nM) and WT amplified to a count of 2±1 (same dilution) at a concentration of 0.17±0.05 nM.

Determining the Interaction Between Biologic Structure and Biodegradable Material The interaction between a specific biologic structure and a biodegradable material enables one to recognize and later modify the material and or biologic structure as needed. The use of titer counts (FIG. 18) and immunochemistry are just a few examples of methods available to determine the interaction between PLGA and peptide. As an alternative, fluorescent immunochemistry was not used because PLGA auto fluoresces at the same emission wavelength as fluorescein (520 nm). Instead, visualization using atomic force microscopy (AFM) was used (FIG. 19).

Titer counts. At least about $1 \times 10^8$ pfu of phage were added to the material (e.g., PLGA). The material was washed at least about five times with 1 mL of 0.1% TBS-T. Non-specific phage was removed by eluting material with 500 μLglycine-HCl (pH 2.2) for at least about nine minutes. For comparison titer counts were obtained from PLGA-predominant phage, WT, and random phage.

Figure 18:
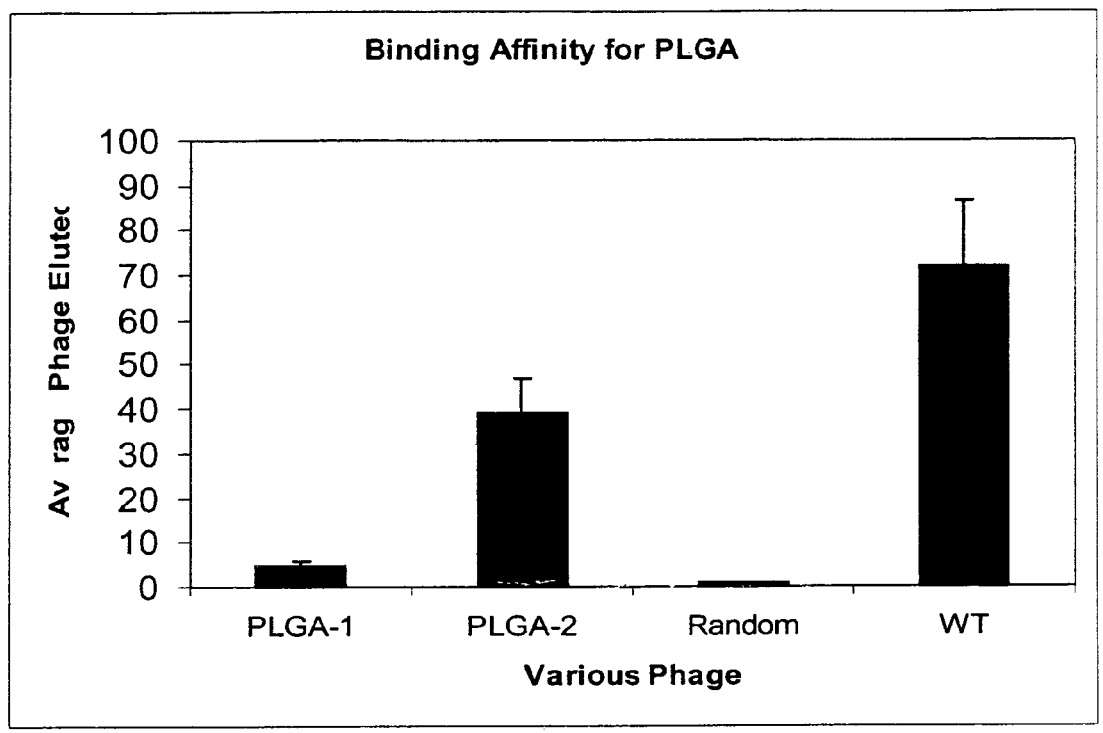
FIG. 18 shows the binding affinity of phage selected for PLGA, where the PLGA-1 sequence is SFPDTYVRVKPA (SEQ ID NO.:7), the PLGA-2 sequence is KPLHSNKYYDRY (SEQ ID NO.:15), and the random sequence is IEHPKTPDSHSR (SEQ ID NO.:4) in accordance with the present invention.
Figure 19:
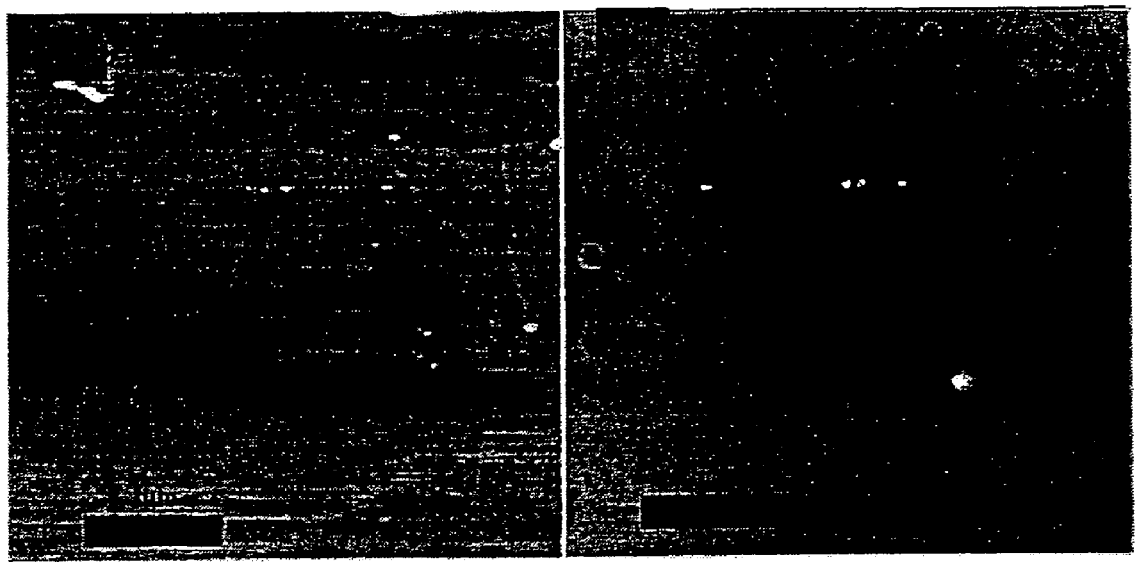
FIG. 19 include AFM images of (A) PLGA-1 phage bound to a material after several washes, where the scale bar represents 1 μm, and (B) WT on PLGA, where samples are 4 μm×4 μm with a z-scale of 20 nm.

FIG. 18 shows that random phage have the lowest recovery with an average count of 1±1 phage, because the random phage is not specific for PLGA. PLGA-1 was found to bind better than the random phage (average count of 5±2 phage). PLGA-2 affinity was higher (average count of 39±4 phage) and WT had an average count of 72±10 phage.

AFM Imaging. Qualitative analysis of phage interactions with the material were performed using AFM. PLGA interacted with $1 \times 10^8$ pfu of PLGA-1 and WT for at least about 1 hour at room temperature. The material was then washed at least about five times with 1 mL of 0.1% TBS-T and then mounted on AFM discs for visualization. The AFM was equipped with a Digital Instruments Bioscope mounted on a Zeiss Axiovert 100s-2tv, operating in tip scanning mode with a G scanner. Images were taken in air using tapping mode. Etched silicon probes with 125-μm cantilevers were used with spring constants of at least about 20-100 N/m driven near their resonant frequency (200-400 kHz). Scan rates were of the order of 1-5 μm/s. Images were leveled using a first-order plane fit to remove sample tilt.

PLGA-1-specific phage were selected and qualitatively analyzed for binding specificity. FIGS. 19A and B show the AFM images. Peptides that are expressed on the phage permit binding to the material via a specific molecular recognition event. If the phage did not have the ability to bind to the material, they would have been removed during washing with 0.1% TBS-T. FIG. 19B shows the absence of phage on the WT sample indicating that any binding is nonspecific.

The present invention may be used to find material-specific biologic structures subsequently used for tissue engineering applications or as drug delivery vehicles in mammals, as examples of their use. The biomaterial with a bi-functional linker may be used to dominate or merely represent one or more biologic structures of interest at the material surface. The bi-functional linker, such as a peptide or other biologic structure, is one with two "sticky" ends, one of which binds to the material and the other to another biologic structures or, alternatively, to another biologic structure. Layered biomaterials may be subsequently constructed if so needed. Importantly, many of all parts of the present invention may be automated with ease.

Independent synthetic peptide or peptide analogs with specific recognition and binding to a biomaterial can also be made with or without linker groups that can be conjugated to RGB or other recognition units based upon the peptide sequences identified through, for example, phage display screening. Additionally, the independent peptides may be made through chemical or biological synthetic routes and would allow the same function, or enhance function, as seen during viral discovery of such peptides. References in the literature describe examples where a peptide identified as a positive binding recognition sequence when bound to a virus can be then used without the virus. See, e.g., (1) Rozinov M. N., Nolan G. P., Evolution of peptides that modulate the spectral qualities of bound, small-molecule fluorophores. Chem Biol. 1998 December; 5(12):713-28.

(2) Venkatesh N, Zaltsman Y, Somjen D, Gayer B, Boopathi E, Kasher R, Kulik T, Katchalski-Katzir E, Kohen F. A synthetic peptide with estrogen-like activity derived from a phage-display peptide library. Peptides. 2002 March; 23(3):573-80.

(3) Petrenko V A, Vodyanoy V J. Phage display for detection of biological threat agents. J Microbiol Methods. 2003 May; 53(2):253-62.

Figure 20:
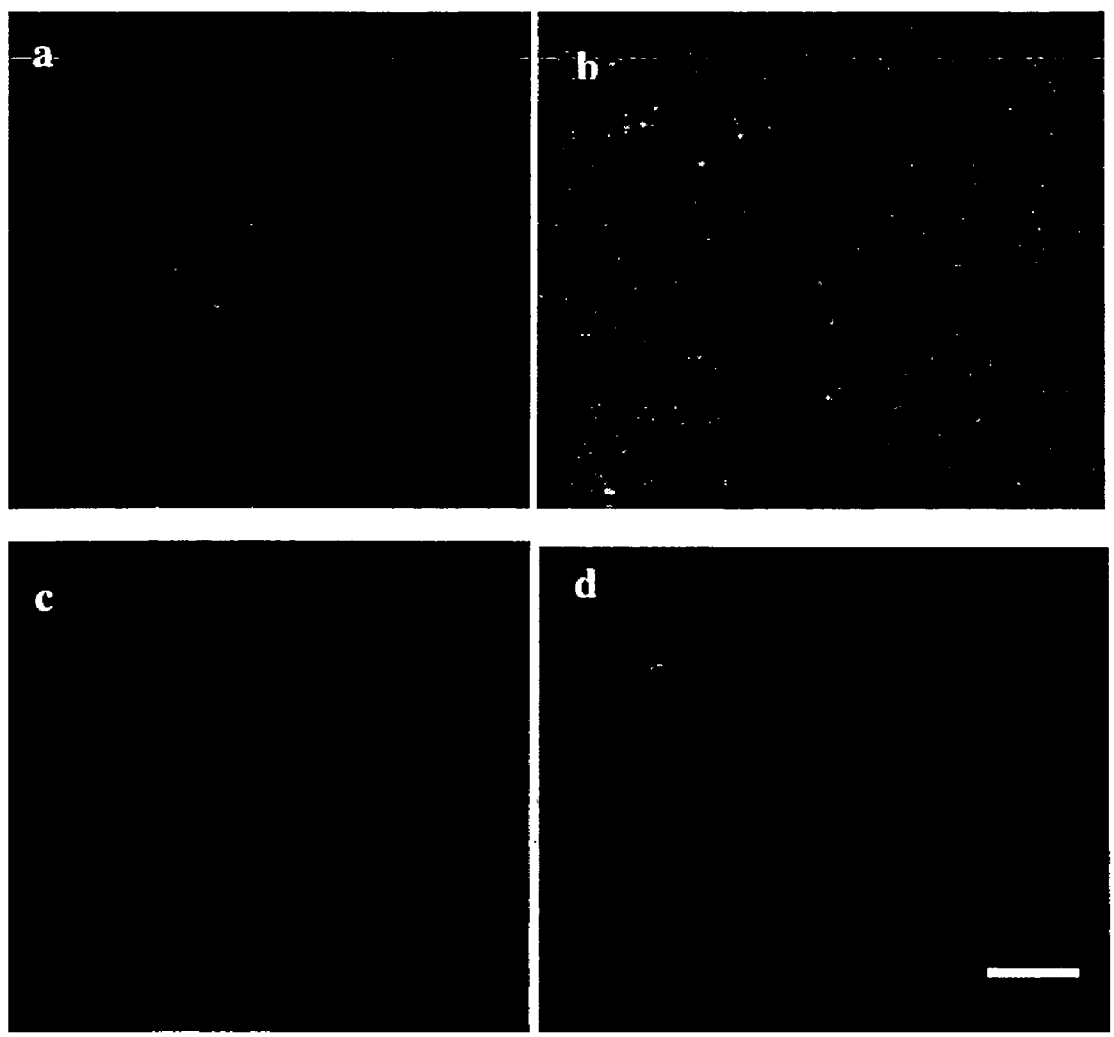
FIG. 20 demonstrates that T59 peptide (SEQ ID NO. 1, THRTSTLDYFVI) (synthesized from the sequence from the T59 phage) binds to PPyCl and not to PPyPSS or to polystyrene (PS). Binding was studied using biotinylated T59 peptide and streptavidin-FITC labeling. (a) control substrate in which no T59 peptide was added. (b) 15 μM peptide bound to 0.5×0.5 cm² PPyCl substrate. (c) 15 μM peptide bound to 0.5×0.5 cm² PPyPSS substrate. (d) 15 μM peptide bound to 0.5×0.5 cm² polystyrene (PS) substrate. All samples were incubated with equal concentrations of streptavidin-FITC. Bar, 10 μm.

Additional working example data were obtained for the polypyrrole system. A peptide was synthesized whose sequence was determined from the T59 phage (ie., SEQ ID NO. 1). Binding assays were performed to determine if the peptide on its own binds to PpyCl without the presence of the phage. The results are provided in FIG. 20 and demonstrate that the T59 peptide binds specifically to PPyCl when compared to PPyPSS (polystyrene sulfonate)doped polypyrrole, and polystyrene (PS).

Figure 21:
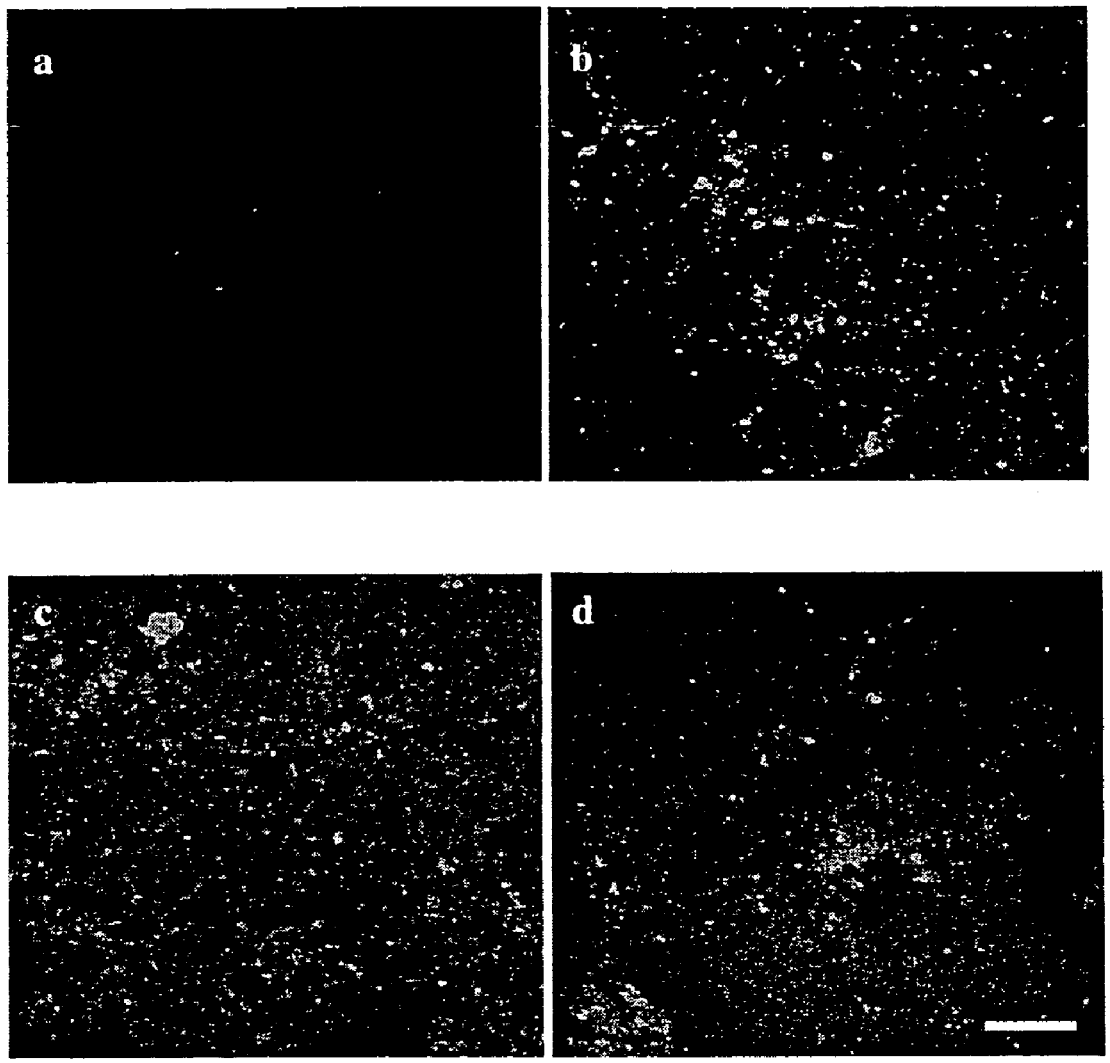
FIG. 21 shows PPyCl-bound T59 peptide (SEQ ID NO. 1) is stable under in serum-containing medium. Binding was studied using biotinylated T59 peptide and streptavidin-FITC labeling. (a) control substrate in which no T59 peptide was added, 0.5×0.5 cm2 PPyCl substrates (b) and (c) were incubated with 15 μM peptide, the samples were then placed in serum-containing media (pH 7.4 and 15% serum) for 3 hr (b), 7 days (c), and 3 weeks (d). Bar, 10 μm.

In addition, T59 peptide binding stability in serum-containing medium was also evaluated in working examples using immunofluorescence (note that all previous experiments were done in saline buffer). The results, presented in FIG. 21, illustrate that a significant fraction of T59 peptides remained bound to PPyCl even after 3 weeks of incubation in serum-containing medium, suggesting a strong and stable interaction between the T59 peptide and the PPyCl surface.

Figure 22:
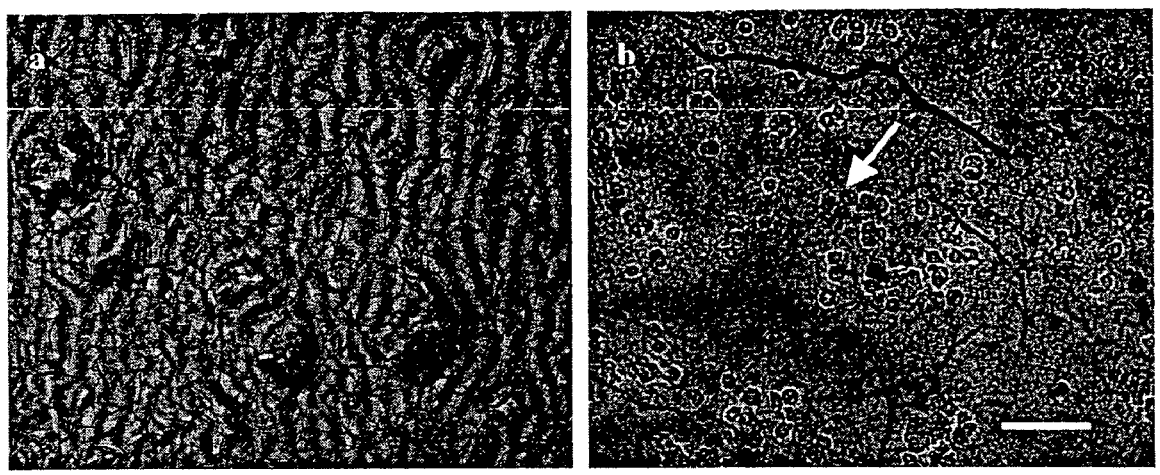
FIG. 22 depicts that T59 peptide (SEQ ID NO. 1) modified with GRGDS (SEQ ID NO: 23) promotes PC12 cell adhesion in serum-free environment on PPyCl. Incubation of ~10⁶ cells/sample, (a) in serum-free media without T59-RGD (SEQ ID NO: 24) on PPyCl, and (b) 60 μM of T59-RGD peptide (SEQ ID NO: 24) was interacted on 0.75×0.75 cm² PPyCl surface, in serum-free media cell adhesion was promoted. Bar, 10 μm.

Finally, PPyCl-specific T59 peptide was modified at the C-terminus with the cell adhesion promoting laminin-derived peptide, RGD, to study cell adhesion in working examples. The results shown in FIG. 22 illustrate that T59-RGD (SEQ ID NO: 24) modified PPyCl promoted cell adhesion when compared to unmodified PPyCl. These studies demonstrated the use of T59 peptide for biomimetic design of PPyCl for tissue engineering applications where the control of cell adhesion and migration is important.

The M.A. thesis by Kiley Preston-Halfmann Miller entitled "Fabrication of Novel Interactive Biomaterials via Peptide Integration for Tissue Engineering Applications" (University of Texas) is hereby incorporated by reference in its entirety. This thesis includes sections on: Introduction (Chapter 1); Peptide Selection (Chapter 2); Chlorine Doped Polypyrrole (Chapter 3); Poly(lactic acid-co-glycolic acid) (Chapter 4); and Conclusions (Chapter 5). Citation to 36 references is provided on pages 55-57 which provides further guidance in the practice of the present invention.

While this invention has been described in reference to illustrative embodiments, the descriptions are not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. An engineered bifunctional peptide comprising:

a first peptide binding domain with length of about 7 amino acids to about 30 amino acids which binds selectively to a biomaterial wherein the first peptide binding domain is defined as a peptide amino acid sequence selected from the group consisting of the amino acid sequence of SEQ. ID. NOS.: 1-22;

a second peptide binding domain with length of about 7 amino acids to about 30 amino acids which binds selectively to an electrically conductive polymer comprising polypyrrole; and a linker joining together the first and second peptide binding domains;

wherein selective binding means that the first and second peptide binding domains include a sequence from a peptide that is not removed during washing with Tris-buffered saline containing 0.1% (vol/vol) Tween-20 (0.1% TBS-T) while bound to the biomaterial or electrically conductive polymer.

2. The engineered bifunctional peptides recited in claim 1, wherein the biomaterial is a biodegradable material.

3. The engineered bifunctional peptides recited in claim 1, wherein the first peptide binding domain is defined further as a peptide which binds non-covalently.

4. The engineered bifunctional peptides recited in claim 1, wherein the biomaterial is selected from the group consisting of a nucleic acid, peptide, and protein.

* * * * *

UNITED STATES PATENT AND TRADEMARK OFFICE
CERTIFICATE OF CORRECTION

| | | |
|---|---|---|
| PATENT NO. | : 7,598,344 B2 | Page 1 of 1 |
| APPLICATION NO. | : 10/654623 | |
| DATED | : October 6, 2009 | |
| INVENTOR(S) | : Angela M. Belcher et al. | |

It is certified that error appears in the above-identified patent and that said Letters Patent is hereby corrected as shown below:

Col. 1, lines 12-13, "may have certain rights" should be --has certain rights--.

Signed and Sealed this

First Day of December, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,598,344 B2 | Page 1 of 1 |
| APPLICATION NO. | : 10/654623 | |
| DATED | : October 6, 2009 | |
| INVENTOR(S) | : Belcher et al. | |

It is certified that error appears in the above-identified patent and that said Letters Patent is hereby corrected as shown below:

On the Title page,

[*] Notice: Subject to any disclaimer, the term of this patent is extended or adjusted under 35 U.S.C. 154(b) by 0 days.

Delete the phrase "by 0 days" and insert -- by 2 days --

Signed and Sealed this

Twenty-second Day of June, 2010

David J. Kappos
*Director of the United States Patent and Trademark Office*